US011680900B2

United States Patent
Groves

(10) Patent No.: US 11,680,900 B2
(45) Date of Patent: Jun. 20, 2023

(54) DIGITAL MOLECULAR ASSAYS

(71) Applicant: ILYTICA LLC, San Francisco, CA (US)

(72) Inventor: Jay T. Groves, San Francisco, CA (US)

(73) Assignee: ILYTICA LLC, San Francisco, CA (US)

(*) Notice: Subject to any disclaimer, the term of this patent is extended or adjusted under 35 U.S.C. 154(b) by 770 days.

(21) Appl. No.: 16/493,237

(22) PCT Filed: Mar. 12, 2018

(86) PCT No.: PCT/US2018/022061
§ 371 (c)(1),
(2) Date: Sep. 11, 2019

(87) PCT Pub. No.: WO2018/169885
PCT Pub. Date: Sep. 20, 2018

(65) Prior Publication Data
US 2020/0132600 A1    Apr. 30, 2020

Related U.S. Application Data

(60) Provisional application No. 62/470,303, filed on Mar. 12, 2017.

(51) Int. Cl.
| | | |
|---|---|---|
| *G01N 21/51* | (2006.01) |
| *C12Q 1/6823* | (2018.01) |
| *G01N 33/49* | (2006.01) |
| *C12Q 1/6825* | (2018.01) |
| *G01N 15/06* | (2006.01) |
| *G01N 33/543* | (2006.01) |
| *G01N 21/17* | (2006.01) |
| *G01N 15/00* | (2006.01) |

(52) U.S. Cl.
CPC ........... *G01N 21/51* (2013.01); *C12Q 1/6823* (2013.01); *C12Q 1/6825* (2013.01); *G01N 15/0612* (2013.01); *G01N 33/49* (2013.01); *G01N 33/54306* (2013.01); *C12Q 2563/107* (2013.01); *C12Q 2563/155* (2013.01); *C12Q 2565/601* (2013.01); *G01N 2015/0038* (2013.01); *G01N 2021/177* (2013.01); *G01N 2470/04* (2021.08)

(58) Field of Classification Search
CPC ............ G01N 33/49; G01N 33/54306; G01N 2015/0038; G01N 2021/177; G01N 2470/04; G01N 21/554; G01N 21/6458; G01N 21/648; G01N 33/54346; G01N 2021/6432; C12Q 2563/107; C12Q 2563/155; C12Q 2565/601; C12Q 1/6825
See application file for complete search history.

(56) References Cited

U.S. PATENT DOCUMENTS

| | | | |
|---|---|---|---|
| 7,169,556 B2* | 1/2007 | Park | C12Q 1/6816 536/26.6 |
| 7,397,043 B2 | 7/2008 | Ja | |
| 2003/0092029 A1* | 5/2003 | Josephson | G01N 33/54326 436/526 |
| 2006/0127946 A1 | 6/2006 | Montagu | |
| 2009/0170070 A1 | 7/2009 | Neerken | |
| 2009/0258371 A1 | 10/2009 | Wardlaw | |
| 2010/0178208 A1 | 7/2010 | Xiao | |
| 2010/0285490 A1* | 11/2010 | Dees | G01N 33/54373 435/7.1 |
| 2014/0193839 A1* | 7/2014 | Cunningham | G01J 3/4406 435/7.92 |
| 2014/0243223 A1 | 8/2014 | Duffy | |
| 2014/0256593 A1 | 9/2014 | Szmacinski | |
| 2015/0293084 A1 | 10/2015 | Del Pino González De La Higuera | |
| 2019/0293665 A1 | 9/2019 | Patel | |
| 2021/0318309 A1 | 10/2021 | Groves | |

FOREIGN PATENT DOCUMENTS

| | | | |
|---|---|---|---|
| EP | 2265931 | 12/2010 | |
| JP | 2008157923 | 7/2008 | |
| WO | 2008051287 | 5/2008 | |
| WO | WO-2009126505 A1 * | 10/2009 | ............. B82Y 15/00 |
| WO | WO-2016020391 A2 * | 2/2016 | ......... G06K 9/00147 |
| WO | WO-2016187588 A1 * | 11/2016 | ............. B01J 13/02 |

(Continued)

OTHER PUBLICATIONS

Xiao et al , Single Molecule Biosensing Using Color Coded Plasmon Resonant Metal Nanoparticles, 2010, Anal. Chern., 82, 6308-6314 (Year: 2010).*

(Continued)

*Primary Examiner* — Narayan K Bhat
(74) *Attorney, Agent, or Firm* — Cynthia Hathaway; C. A. Schlecht; Erik Larsen

(57) ABSTRACT

Provided herein are systems, devices and methods for the rapid and accurate measurement of analytes by assay of binding events, by direct, digital measurement of individually resolved analyte/reporter binding events. The digital molecular assay systems, devices and methods disclosed herein are capable of particle-by-particle readout using optical reporter molecules that detect and report the binding of a single analyte molecule, and report each such binding in binary format. Such digital molecular assay systems, devices and methods are useful in a variety of applications, such as on mobile electronic devices for use in the field.

42 Claims, 16 Drawing Sheets

(56) References Cited

FOREIGN PATENT DOCUMENTS

WO   2018169885   9/2018
WO   2021207656   10/2021

OTHER PUBLICATIONS

International Application No. PCT/US2018/022061; International Search Report and Written Opinion, of the International Searching Authority, dated Mar. 12, 2018; 28 pages.
Walt, D., "Optical Methods for Single Molecule Detection and Analysis", Anal Chem., 85(3):1258-63, (2013).
Agrawal, A. et al., "Counting Single Native Biomolecules and Intact Viruses With Color-Coded Nanoparticles", Anal Chem., 78(4):1061-70, (2006).
Fazio, B. et al., "SERS detection of Biomolecules at Physiological pH via aggregation of Gold Nanorods mediated by Optical Forces and Plasmonic Heating", Sci Rep., 6:26952, (2016).
International Application No. PCT/US2021/026660; International Search Report and Written Opinion of the International Searching Authority, dated Jul. 28, 2021; 7 pages.
Schultz, S. et al., "Single-Target Molecule Detection With Nonbleaching Multicolor Optical Immunolabels", Proc Natl Acad Sci USA, 97(3):996-1001, (2000).
International Application No. PCT/US2018/022061; International Preliminary Report on Patentability, dated Sep. 26, 2019; 12 pages.
Levene, M. et al., "Zero-Mode Waveguides for Single-Molecule Analysis at High Concentrations", Science, 299 (5607):682-6, (2003).
International Application No. PCT/US2021/026660; International Preliminary Report on Patentability, dated Oct. 20, 2022; 5 pages.

\* cited by examiner

DIGITAL MOLECULAR ASSAYS

CROSS-REFERENCE TO RELATED APPLICATIONS

This application claims the benefit of priority of U.S. Provisional Application No. 62/470,303, filed Mar. 12, 2017, the disclosure of which is hereby incorporated by reference as if written herein in its entirety.

Point-of-care diagnostics and other assays performable in the field are a pressing need. If the delay and expense associated with sending assays such as diagnostic tests, especially blood tests, to dedicated laboratories for analysis could be eliminated, responses could be made more efficiently and effectively. Clinical laboratories deliver diagnostic tests by performing biochemical assays on precision, benchtop instruments. Efforts to miniaturize these instruments or replicate their function on mobile electronic devices are fraught with difficulty. In many cases the results are unusable.

What are needed are inexpensive, but accurate, point-of-care says such as diagnostic tests that provide quick and accurate results, for example doctors and their patients.

Provided herein are systems, devices and methods for the rapid and accurate measurement of analytes by assay of binding events, by direct, digital measurement of individually resolved analyte/reporter binding events. The digital molecular assay systems, devices and methods disclosed herein are capable of particle-by-particle readout using optical reporter molecules that detect and report the binding of a single analyte molecule, and report each such binding in binary format. Such digital molecular assay systems, devices and methods are useful in a variety of applications, such as on mobile electronic devices for use in the field.

BRIEF DESCRIPTION OF THE DRAWINGS

FIG. 1 represents the reporter volume, 2 represents the surface of a recorder device, 3 represents a reporter molecule, and 4 represents an optical path from reporter molecule to recorder device.

FIG. 1 represents the reporter volume, 2 represents the surface of a recorder device, 3 represents a reporter molecule, 4 represents an optical path from reporter molecule to recorder device, and 5 represents a larger particle that is attached to, or contains, the reporter molecule 4.

DETAILED DESCRIPTION OF THE DISCLOSURE

Figure 1:
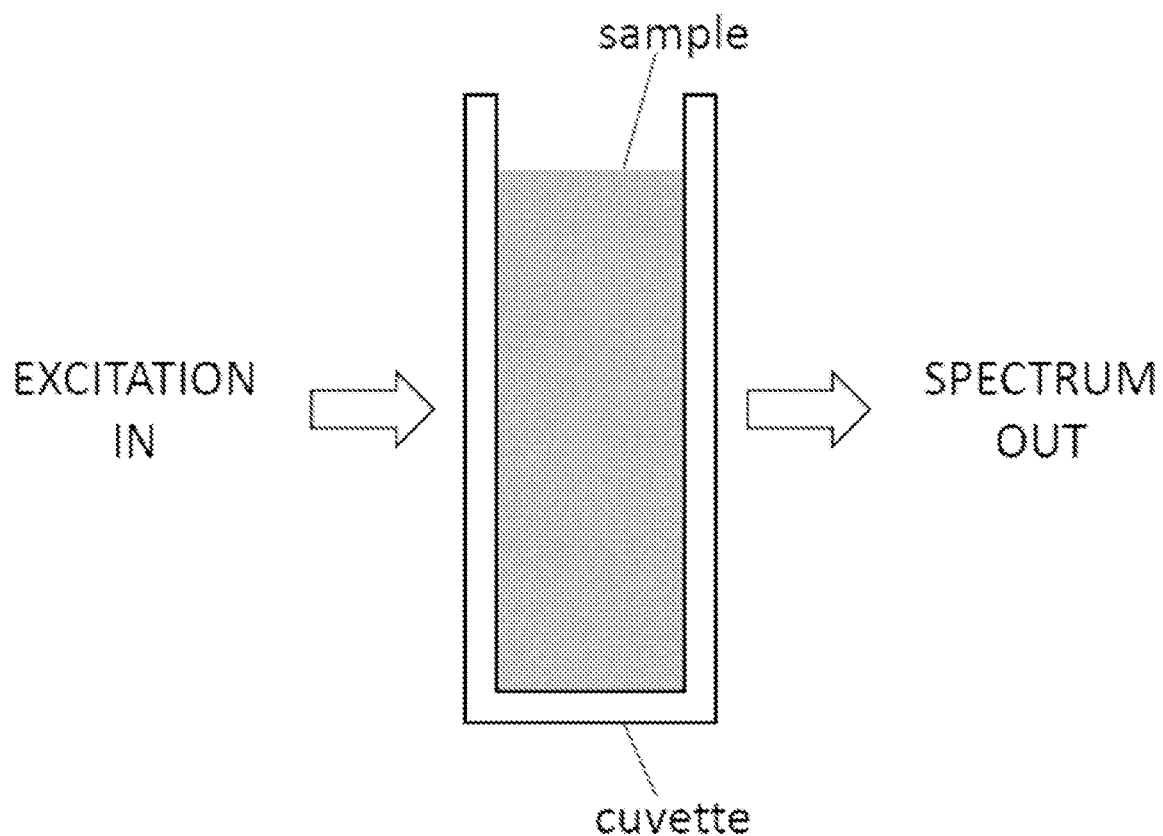
FIG. 1 is a conceptual illustration of an analog assay.

Although there is great demand for performing biochemical assays on mobile electronic devices, attempts to simply miniaturize conventional assays and perform them outside the controlled environment of professional, clinical laboratories have not succeeded in the past. Conventional biochemical assays cannot be reliably miniaturized because they are inherently analog measurements.

Digital assays eliminate inherent uncertainties of analog assays in at least three ways: (1) digital assays are based on binary events that are highly resistant to analog noise; (2) digital assays eliminate errors originating from the unknown fraction of inactive assay molecules in an analog assay; (3) digital assays eliminate problems associated with spatial inhomogeneity such as non-uniform illumination.

Consider, for example, an antigen-antibody assay designed to measure the concentration of antigen in a sample that is mixed with a known concentration of antibodies. The assay has an optical readout in which antibodies that bind antigen emit a different optical signal than those that do not. (Unbound antibodies might emit no signal, for example.) Given the affinity of antigen-antibody binding, a bulk optical readout signal may be used to estimate antigen concentration.

This procedure can be made to work reasonably well in a professional laboratory setting with strict quality controls. It fails miserably, however, when performed with mobile devices in a field setting. Conventional, analog biochemical assays are delicate and give wildly inaccurate results when performed on cell phones, tablets, and similar devices.

One problem is that without strict laboratory protocols a large fraction of the supposedly known concentration of antibodies may be inactive. In a field setting anywhere from 10% to 100% of the antibodies may be rendered inactive due to improper handling, contamination, denaturation and other problems. Worse, the fraction of inactive antibodies is unknown. It is unobservable and represents a systematic error that cannot be eliminated by averaging observed data. The fraction of unbound antibodies and the fraction of inactive antibodies is confounded; their signals are indistinguishable.

Digital assays reduce or eliminate this problem by counting individual binding events between analyte and reporter molecule, such as antigen and antibody or complementary nucleotide sequences, rather than averaging the results of millions of them. Mobile devices are well suited for digital assays because they include high quality cameras capable of sampling millions of biochemical events—as many as one per pixel or tens of millions per exposure. Mobile devices also include significant processing power for image analysis and communication capabilities for reporting results and offloading processing if necessary.

Digital assays select features in an image and classify them as valid or null. Null features include anything in an image that does not meet specific criteria for position, brightness, wavelength or shape, for example. Inactive antibodies are a common source of null features, but irregular sample illumination, imprecise optical alignment, sample irregularities—all common problems in a mobile setting and in other scenarios with inadequate controls—also contribute. In a digital assay, null features are discarded for data analysis; only valid features contribute to assay results. Valid features are counted as bound or unbound, and those are the only possibilities. Yes or no; one or zero. If, in a digital assay, 463 valid features are counted as bound and 886 features are counted as unbound, then the bound fraction is 463/(463+886)=463/1349=0.343. This kind of result comes from a digital process. When it is combined with known analyte binding affinity, it provides the desired analyte concentration. The fraction of events classified as null makes no difference in the result.

It is helpful to keep in mind that it is the assay itself that is digital. This concept has nothing to do with the ubiquitous digitizing of analog results. Signals produced by analog assays may be digitized for analysis or storage, but digitizing an analog signal cannot remove systematic errors that are "baked in" to it. As an analogy, musical recordings made with analog equipment retain static pops and hiss—inseparable from the music in an analog recording process—even if the recording is stored digitally.

Turning now to the figures, FIG. 1 is a conceptual illustration of an analog assay. A cuvette contains a sample. The sample may be a solution containing antigen and antibodies, for example. The antibodies may be labeled so that, upon binding an antigen molecule, the newly formed antigen-antibody complex emits an optical signal when interrogated by an optical excitation. The optical signal may be a spectral measurement; i.e. light intensity versus wavelength. The cuvette, even though it may hold a small sample volume, just a few milliliters is a common size, contains many billions of antibodies and antigen molecules. The observed spectrum is a composite of spectra emitted by billions of bound, labeled antigen-antibody complexes. But, an unknown fraction of the antibodies don't work; they can't bind antigen because they are jammed up in aggregates, denatured or have other problems.

Figure 2:
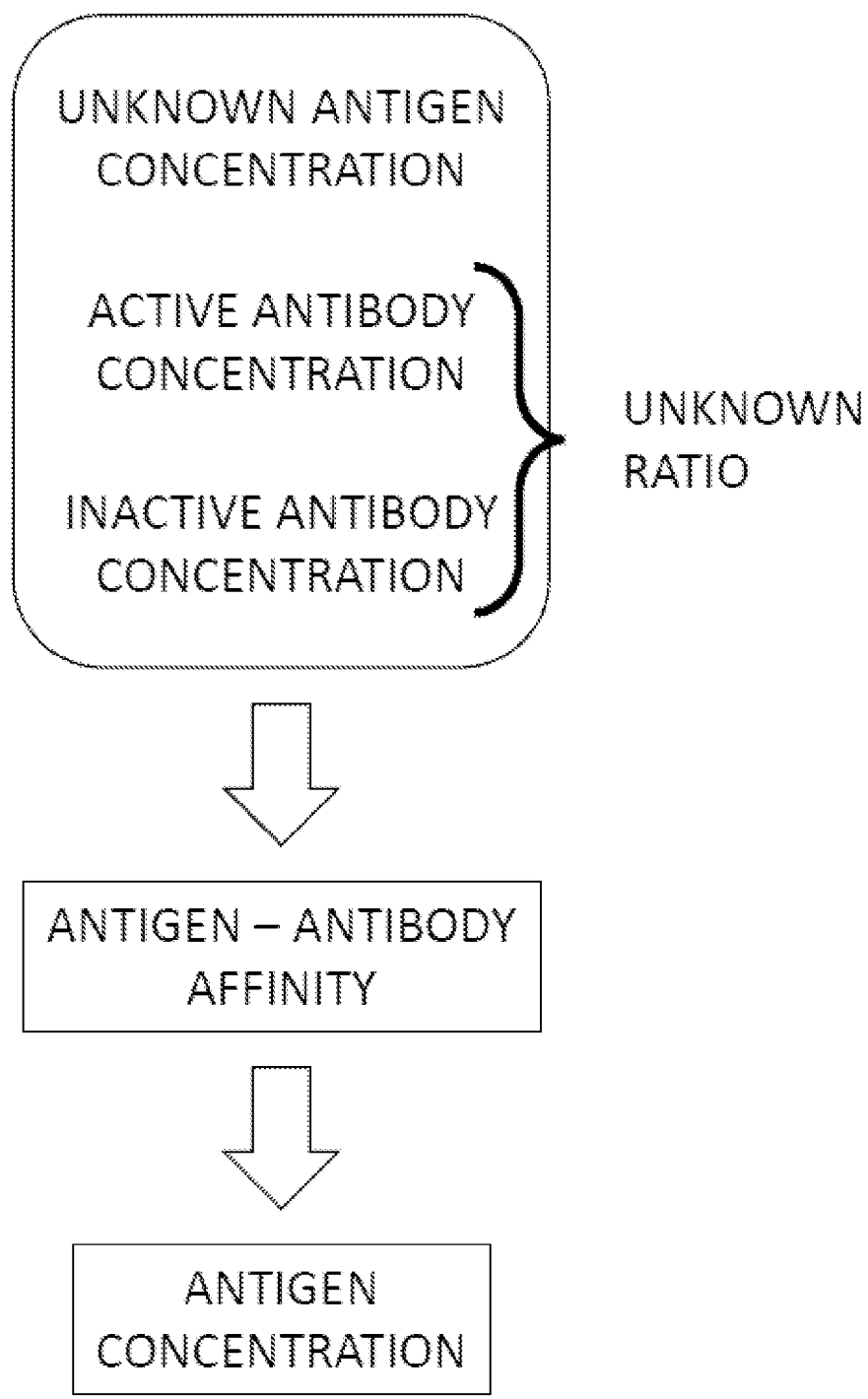
FIG. 2 is a conceptual diagram of analog assay procedures.

FIG. 2 is a conceptual diagram of analog assay procedures. The assay begins with an unknown antigen concentration mixed with an antibody concentration. The ratio of active antibodies (ready and able to bind antigen) to inactive antibodies (unable or unavailable to bind antigen) is not known. In a professional laboratory setting, trained technicians following strict procedures in a controlled environment can keep the active-to-inactive ratio high or at least consistent. In a field or point-of-care setting, however the ratio of active-to-inactive antibodies is much lower and, worse, totally inconsistent.

Active antibodies bind antigen at a rate determined by: the antigen-antibody affinity, the concentration of antigen, and the unknown concentration of active antibodies.

Figure 3:
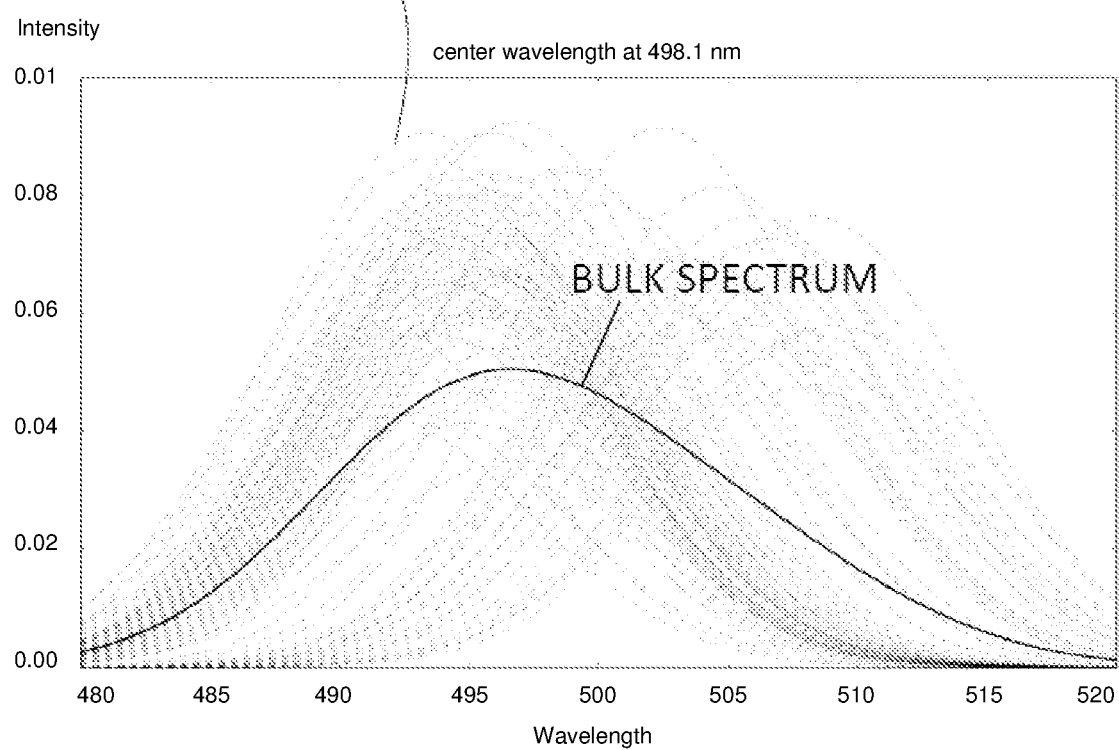
FIG. 3 is a simulation of analog assay results.

FIG. 3 is a simulation of analog assay results. The bulk spectrum (heavy solid curve) represents what is observed ("SPECTRUM OUT") in an analog assay. The numerous, light dashed curves represent spectra from single antigen-antibody binding events. These spectra are not observable in an analog assay, however. In the simulation of FIG. 3, unbound, active antibodies emit light around 495 nm wavelength while bound, active antibodies emit light around 505 nm wavelength. An unknown number of inactive antibodies do not emit light. This means that the bulk spectrum does not provide sufficient information to measure the number of bound antibodies as a fraction of all active antibodies.

The situation is worse in an actual experiment because inactive antibodies may still emit light, but that light provides no information about antigen binding. It just contributes to systematic error.

Figure 4:
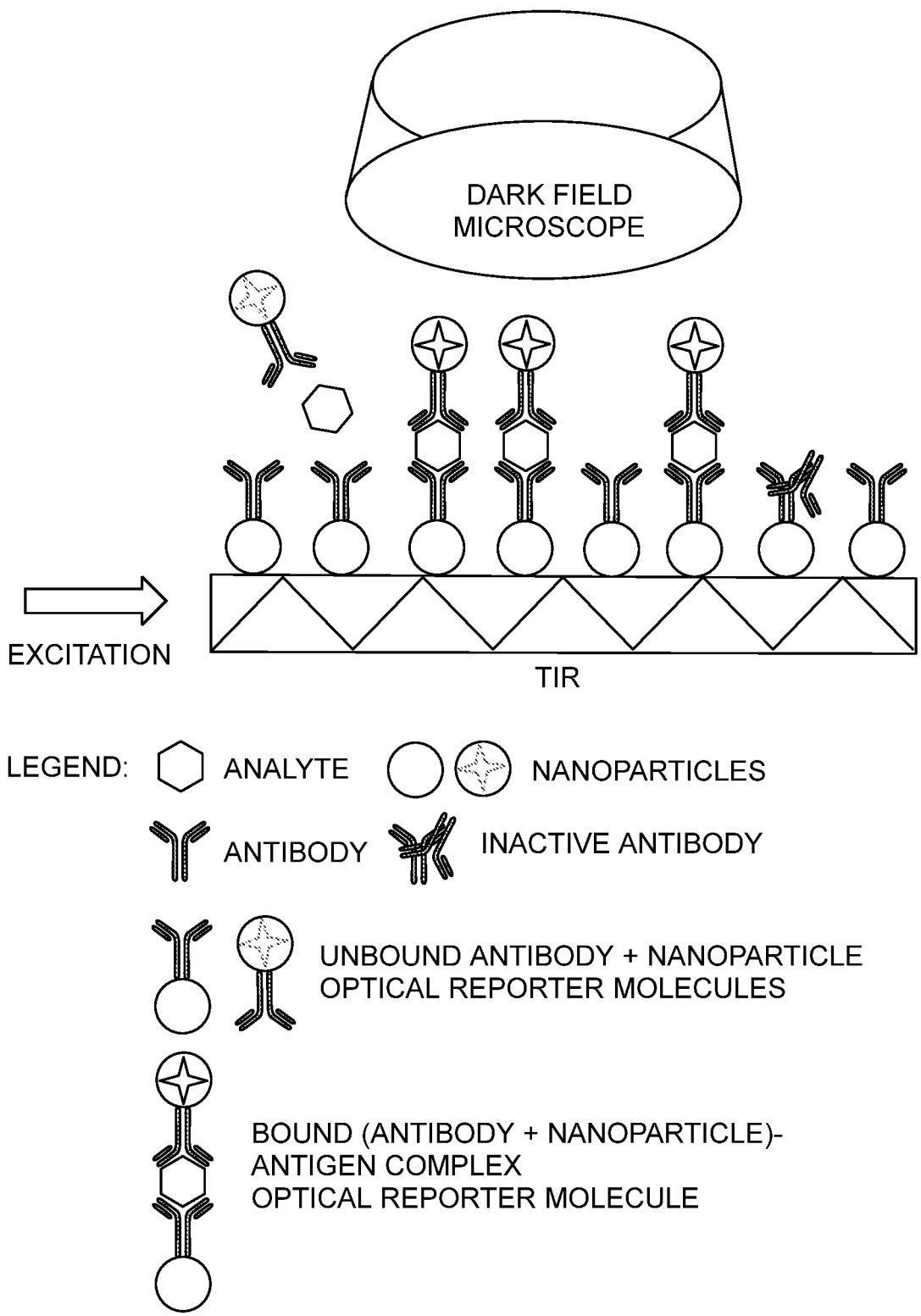
FIG. 4 is a conceptual diagram of part of a digital molecular assay system.

FIG. 4 is a conceptual diagram of part of a digital molecular assay system. The digital molecular assay illustrated in FIG. 4 depicts an example wherein mobile dark-field microscopy performed with a smartphone camera, for example, captures an image of a plasmonic nanoparticle sandwich-type immunoassay. In this assay, a total internal reflection (TIR) substrate is coated with plasmonic nanoparticles functionalized with capture antibodies designed to bind an antigen of interest. Additional plasmonic nanoparticles, functionalized with the same or different antibodies (i.e., designed to bind an equivalent part of the antigen, or a different part) are introduced, along with the antigen of interest in a sample. Excitation light is introduced into the substrate from an edge. Bound antibodies emit different optical signals than unbound and inactive antibodies. Antibodies may be inactive due to many factors, such as degradation or, more commonly, aggregation. The differing signals may appear in an image as different sizes, brightness, spectra, shapes, et cetera, and be sorted as active or null considering one or more of these factors.

Figure 5:
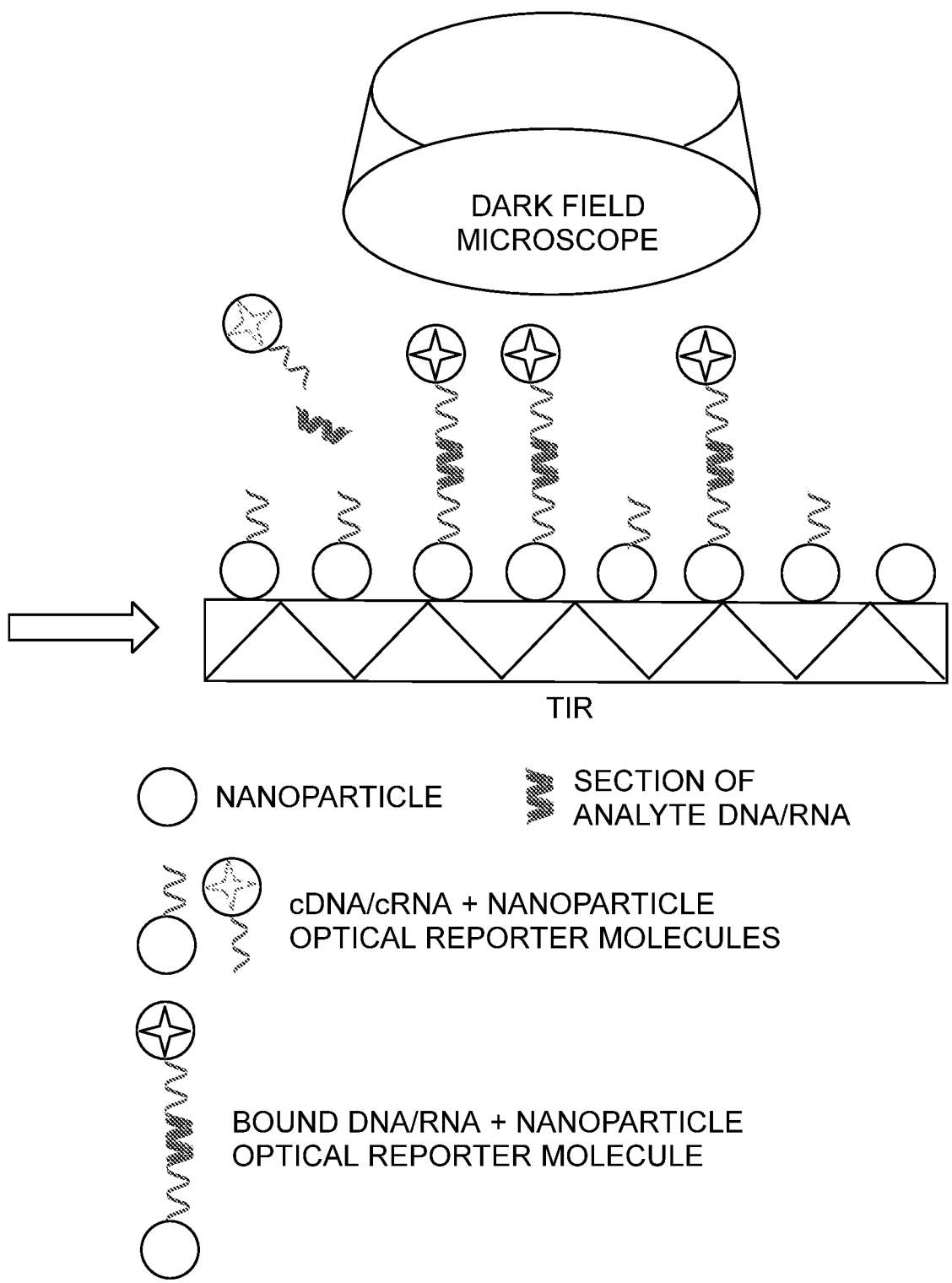
FIG. 5 is a conceptual diagram of part of an alternate digital molecular assay system.

FIG. 5 is also a conceptual diagram of part of a digital molecular assay system; it is an alternative of the example above wherein the TIR substrate is coated with plasmonic nanoparticles functionalized with capture nucleotide sequences of DNA or RNA, complementary to part of the analyte DNA/RNA of interest. Additional plasmonic nanoparticles, functionalized with different cDNA/cRNA (i.e., designed to bind another section of the analyte DNA/RNA) are introduced, along with the analyte DNA/RNA in a sample. Bound DNA/RNA sequences emit different optical signals than unbound and inactive antibodies.

Figure 6:
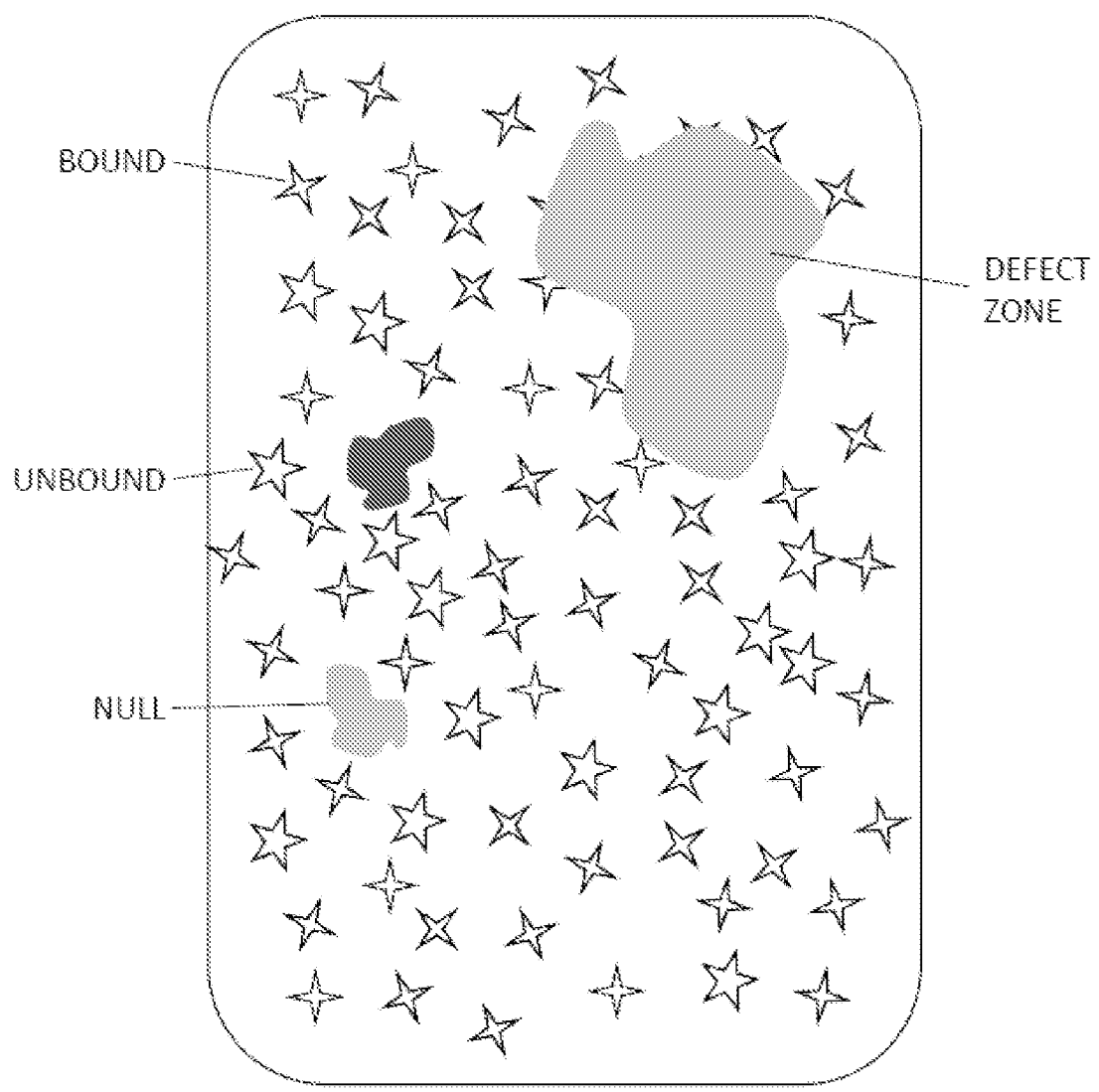
FIG. 6 is a conceptual diagram of digital molecular assay image data.

FIG. 6 is a conceptual diagram of digital molecular assay image data; i.e. part of an image captured by a mobile device camera operating as a dark field microscope. The image includes spots produced by bound antigen-antibody complexes, spots from unbound antibodies, spots from inactive or null antibodies and a defect zone which may be an area of the image that is defective for any of a number of reasons. Illumination of the image may be non-uniform, even far from uniform. As long as the spatial illumination pattern is known, by recording an image at the illumination wavelength, for example, results at any point in the image may be normalized to the known illumination.

Figure 7:
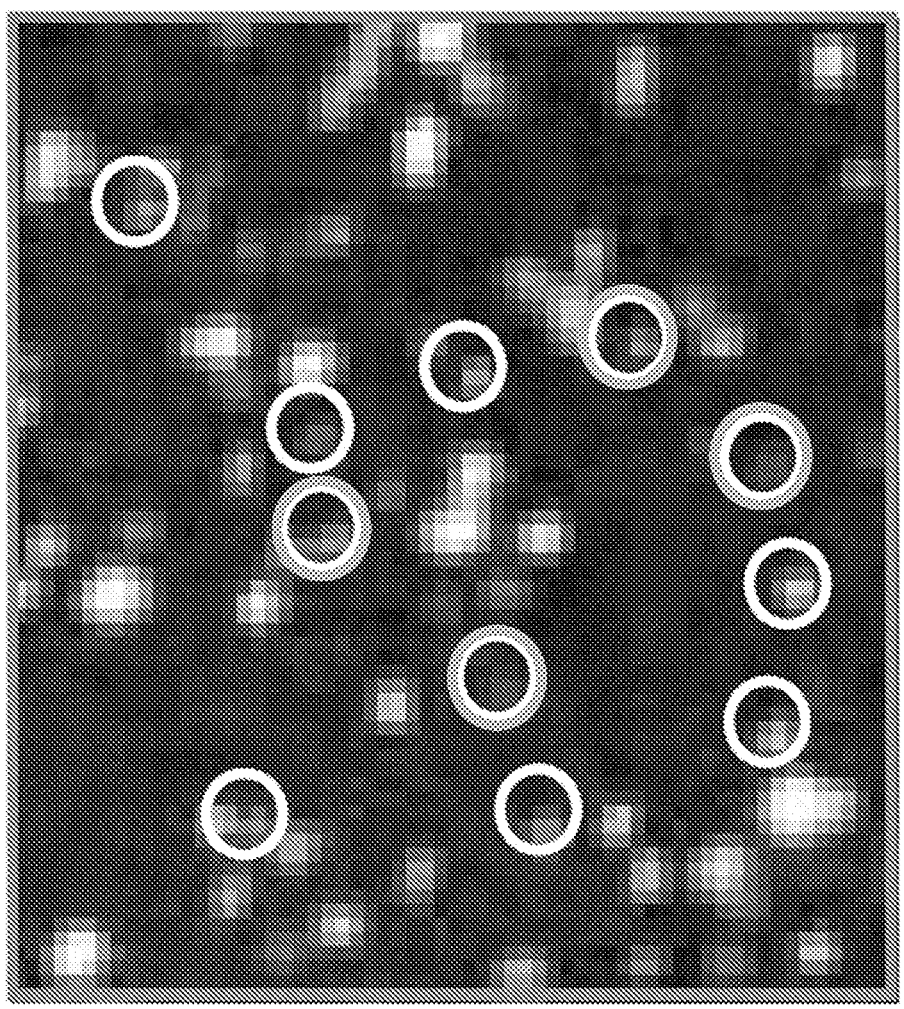
FIG. 7 is an image of digital molecular assay data.

FIG. 7 is a depiction of digital molecular assay data obtained by a mobile device camera operating as microscope. The figure is less impressive when shown in grayscale as it is in this disclosure compared to the original color image, so it has been manually enhanced for submission in black-and-white. White circles have been drawn around spots in the image that correspond to active antibodies. All other spots in the image are null or inactive antibodies. Of the active antibodies, 4 out of 11 are bound; these are depicted by way of example with a gray circle around the white one. The identification of active versus null, and bound versus unbound is performed by image analysis software. Image analysis may be performed on the mobile device. Alternatively, the mobile device may send the image to another processor. It may send the image to a virtual server in the computer cloud, for example.

Figure 8:
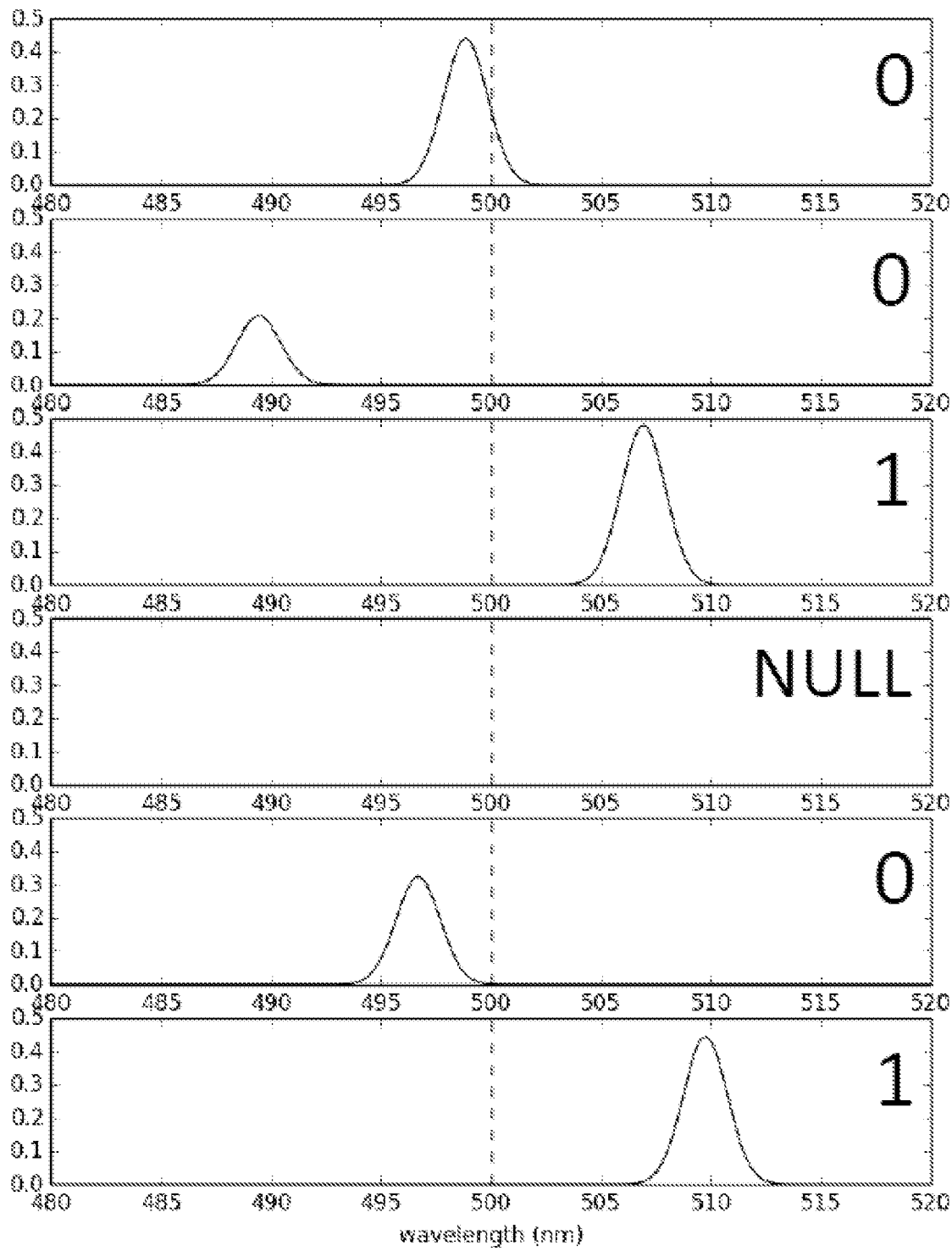
FIG. 8 is a simulation of digital molecular assay results.

As an example of image processing to distinguish bound from unbound antibodies in a digital molecular assay, FIG. 8 is a simulation of digital assay results. FIG. 8 represents spectra from six spots in an image from a digital assay. The criteria for bound versus unbound is whether the spectrum from a spot lies above or below 500 nm in wavelength. Spots with spectra that do not fall in the range shown in the figure are null. From top to bottom, the spectra correspond to spots from unbound, unbound, bound, inactive (null), unbound and bound antibody sites. There are two positive results, three negative and one null. Thus the fraction of bound antibodies is ⅖. As mentioned above, an actual experiment is complicated by optical signals from inactive antibodies. Thus the selection criteria may be more complicated than spectral center above or below a certain wavelength. The criteria may involve narrow spectral bands, intensity criteria, spectral shape, and spatial shape as examples.

The selection criteria also take into account knowledge of a spatial illumination pattern. Intensity measured at an emission wavelength is normalized by illumination intensity at an excitation wavelength at the same location in an image. This eliminates problems of spatial inhomogeneity which plague analog measurements. The assay proceeds digitally on a particle-by-particle basis considering "EXCITATION IN" and "SPECTRUM OUT" for each particle. The result for a given particle can only be 0 or 1.

Figure 9:
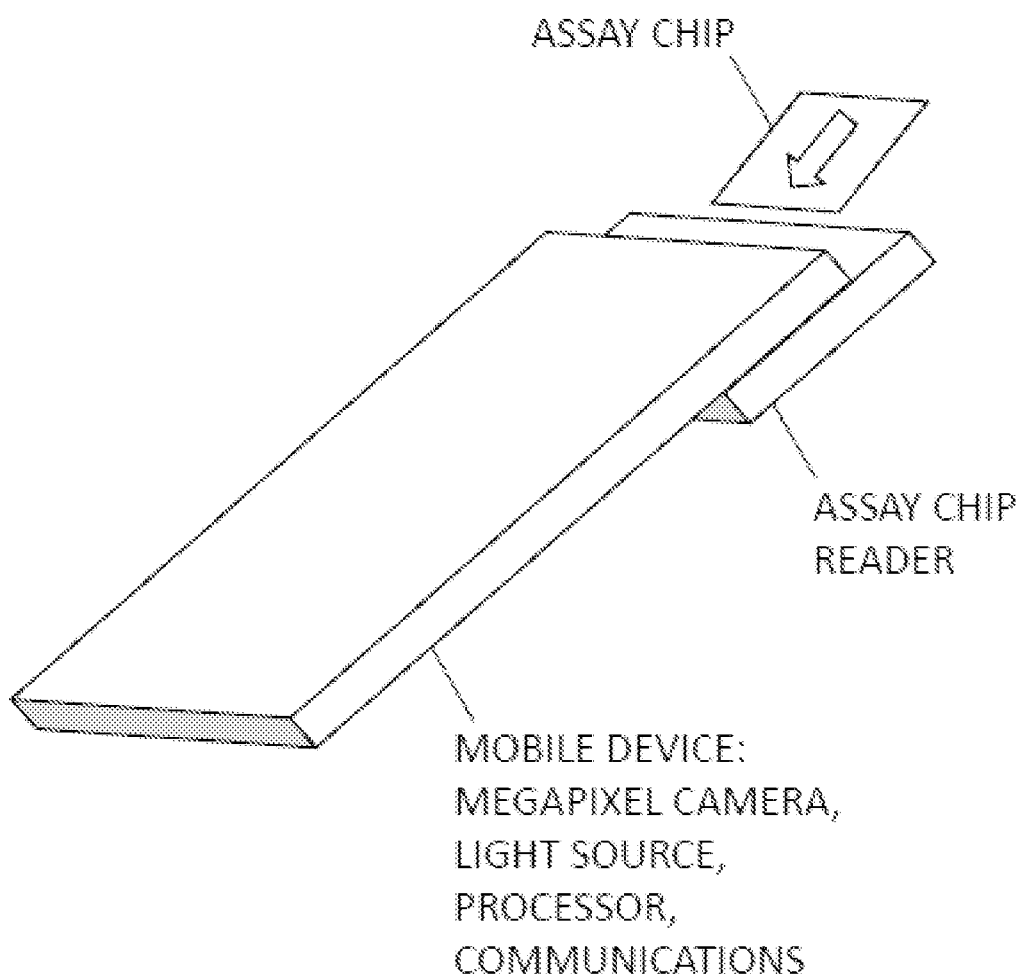
FIG. 9 shows a mobile electronic device with a clip-on assay chip reader.

Digital molecular assays may be performed with mobile devices as illustrated in FIG. 9 which shows a mobile electronic device with a clip-on assay chip reader. The assay chip reader may include optical components that adapt the mobile device camera for dark field imaging, for example. The assay chip is designed to receive analyte solution and may be pre-coated with antibodies.

Figure 10:
FIG. 10 illustrates codes that may be embedded in a digital molecular assay.

Since a digital assay is based on imaging and image analysis, codes may be placed on an assay chip and read out from the same images used to measure binding events. FIG. 10 illustrates codes that may be embedded in a digital assay. Examples include bar codes, quick response (QR) codes, quantum dots that emit light at engineered wavelengths, nanoparticle reporters of temperature, humidity, light exposure, gas exposure and other environmental data. Identifying marks representing particular assay types or sample identification may also be included.

The examples discussed above are presented using antigen-antibody binding. Antigen and antibodies may be linked to optical reporter molecules for assay readout. Assays involving other cross-linking mechanisms may also be performed digitally. For example, assays based on hybridization of DNA or RNA fragments bound to optical reporter molecules may be performed as digital molecular assays where complementary DNA or RNA fragments take the place of antigen and antibody molecules. As an example, a first part of a short DNA sequence may be bound to an optical reporter and a second part of the short DNA sequence may be bound to another optical reporter. When the first and second part bind to a longer, complementary DNA sequence, the two optical reporters are brought close together and therefore emit a different optical signal compared to when they are farther apart. This kind of assay may be used to detect the complementary DNA sequence.

In conclusion, it is a fool's errand to use a mobile device as a surrogate for professional laboratory instrumentation with analog assays. Digital molecular assays allow particle-by-particle readout of individual interactions between single analyte molecules and reporter molecules, rendering irrelevant the practical problems attendant with traditional assays. Leveraging the imaging and image processing capabilities of mobile devices to provide diagnostic results that reduce or eliminate common sources of systematic errors found in analog assays, digital molecular assays enable in-field assessments such as point-of-care diagnostic tests that help doctors and patients obtain critical health information quickly and inexpensively, and the collection and analysis of data across a wide range of applications.

Terms and Definitions

Unless defined otherwise, all technical and scientific terms used herein have the same meaning as commonly understood by one of ordinary skill in the art to which this invention belongs.

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "accuracy", as used herein, alone or in combination, is used to refer to the closeness of a reported or estimated value from the true value. An inaccurate measurement, observation, or estimation deviates from the true value. An accurate measurement, observation, or estimation does not deviate from the true value.

The term "analyte", or "analyte molecule", as used herein, alone or in combination, is used to describe a molecule or particle for which the presence or absence, or amount, in a sample is originally unknown, and for which knowledge of the presence or absence, or amount, contained in a sample would be useful. Examples of analytes include biomolecules, such as: peptides, proteins, cytokines, and prions; antibodies, and fragments thereof; nucleic acids (DNA/RNA) and particles containing them, such as histones; small organic and bioinorganic molecules, such as carbohydrates, lipids, hormones, and intermediates and products of metabolism; macromolecules, such as macrocycles, biopolymers (e.g. oligosaccharides, polyphenols, and plastics); and viruses, viral particles, viral products (e.g. virokines). An analyte may also be categorized as a biomarker, that is, a composition and/or molecule or a complex of compositions and/or molecules that is associated with a biological state of an organism (e.g., a condition such as a disease or a non-disease state) and can report the presence of disease, injury, or cellular or organismal damage. When such markers bind to an antibody or a fragment thereof, they may be referred to as antigens. Values for meaningful (e.g., normal and abnormal) levels of analytes detected by the digital molecular assays disclosed herein will be known to those of skill in the relevant art.

The term "area detector", as used herein, alone or in combination, refers to a recording device that can record an image from a source, i.e., record not only the intensity of an incoming optical signal, but the origin of an optical signal. Common examples of area detectors are television cameras, digital SLR cameras, and cellphone cameras.

The term "assay chip", as used herein, alone or in combination, refers to a microarray of reporter molecules (e.g. optical reporter molecules) spotted or otherwise deposited onto a reporter surface, optionally enclosed within a relatively thin, flat cuvette such as a slide, which can be exposed to a sample containing analyte such that the interaction between the capture elements of the optical reporter molecules and the analyte can be observed. Techniques for the production of assay chips are known in the art. An assay chip may comprise optical reporter molecules or plasmonic nanoparticles functionalized with antibodies, proteins, DNA, RNA, etc.

The term "assay chip reader", as used herein, alone or in combination, refers to a system or device for observing and recording signals from an assay chip. An assay chip reader may be part of a digital molecular assay system as disclosed herein, and typically comprises a chamber for receiving an assay chip, a recording device such as an image sensor (e.g., a camera), a means for transmitting the data collected from the assay to memory, and optionally, a light source such as a light-emitting diode (LED). Additionally, the assay chip reader may contain microfluidic hardware such as pumps, channels, chambers for solutions, valves, mixers, and the like; and hardware and/or software for performing at least some analysis of the data. In certain embodiments, an assay chip reader may be coupled with a smartphone or other mobile device and used as part of a portable assay system; miniaturized microplate and chip readers are known in the art.

The term "binding isotherm", as used herein, alone or in combination, refers to the degree of binding of bound reporter molecules to analyte molecules at different concentrations of analyte. In general, the degree of binding, which can be defined as the ratio of bound reporter molecules to total reporter molecules, increases with increased analyte concentration, and eventually approaches 1, as nearly all reporter molecules are bound to analyte molecules.

The term "binning", as used herein, alone or in combination, refers to the combination of signals from two or more pixels into one signal. Binning can be used when spatial resolution can be sacrificed in order to improve signal-to-noise. "2×2 binning", by way of example, refers to the grouping of pixels into 2×2 squares, and summing the signals from the pixels contained in each square.

The term "biomolecule", as used herein, alone or in combination, includes any type of organic or bioinorganic molecule for which detection (either qualitative or quantitative) may be desired, including but not limited to, peptides, proteins, nucleic acids, sugars, mono- and polysaccharides, lipids, lipoproteins, whole cells, and the like.

The term "camera," as used herein, refers to a type of image sensor for recording visual images, for example as digital images. A "megapixel camera" is a camera that can record one million, or multiples of one million, pixels per image. Many smartphone cameras comprise ten-megapixel or more cameras.

The term "communication interface," as used herein, refers to a means for transferring data from a device or system as used herein to another device or system. Examples of wireless communications interfaces include those used in wireless devices such as mobile phones, for example cellular, wi-fi, and Bluetooth technologies.

The term "concentration", as used herein, alone or in combination, refers to the amount of a solute in a solution per unit volume of solution. Concentration can be specified in units of molar concentration, i.e. number of moles of solute per liter of solution, or number concentration, i.e., number of molecules of solute per liter of solution. Molar concentration and number concentration can be readily interconverted. As used herein, the term "concentration" is expanded to include systems outside the traditional definition of "solution", e.g., systems containing molecules tethered to a solid support.

The term "deconvolution", as used herein, alone or in combination, is used to describe a method for determining, from a collective optical signal that is composed of individual optical signals from a plurality of optical reporter molecules, the individual optical signals from the individual optical reporter molecules. Deconvolution can use curve-fitting techniques to determine the individual spectral features from individual optical reporter molecules that partially overlap across a spectral region and that have combined to form a single collective spectrum. Deconvolution can use curve-fitting techniques to determine individual images from individual optical reporter molecules that partially overlap in a spatial region of a detector and that have combined to form a single collective image. It will be understood that deconvolution techniques are particularly useful for small groups of optical reporter molecules.

The term "detect" or "detection", as used herein, alone or in combination, is used to describe a method of determination of the existence, presence, or fact of an analyte in a sample.

The term "divergence" indicates the deviation from perpendicularity that is accommodated by the recording device. An idealized area-detector type recording device will accept only light rays that are perpendicular to the plane of the detector. Actual area detectors will allow light rays that arrive at an angle from the perpendicular. Although this feature can increase signal-to-noise (since more light rays are accepted by the detector), it also decreases spatial resolution, depending on the size of the divergence angle allowed, and the size of the area detector pixel and distance between the area detector and the sample plane.

The term "incubate", as used herein, alone or in combination, is used to describe a process of exposing reporter molecules to a sample that can potentially contain an analyte molecule.

The term "oblong" as used herein, alone or in combination, is used to describe a volume having unequal dimensions. Examples of oblong volumes include prisms or cylinders for which the distance between the end faces is either significantly larger or significantly smaller than dimensions parallel to the end faces. A further example of an oblong volume is an ellipsoid for which one axis is either significantly larger or significantly smaller than the other axes.

The term "optical path", as used herein, alone or in combination, is used to describe the path from reporter molecule to detector.

The term "optical reporter molecule," or, equivalently, "optical reporter," as used herein, alone or in combination, is used to describe a reporter molecule that is capable of reporting either the presence or absence, or the amount or concentration of, an analyte molecule, with an optical signal. The presence or absence of the analyte molecule (optionally, in certain assay formats, with another optical reporter molecule) in contact with the optical reporter molecule, induces a change in the optical signal. An optical reporter molecule bound to analyte ("bound optical reporter molecule") will emit a different signal than an optical reporter molecule not bound to analyte ("unbound optical reporter molecule").

The term "optical signal", as used herein, alone or in combination, is used to describe a signal that originates from an optical reporter molecule. The optical signal may fall in the visible range of the spectrum, or outside the visible range of the spectrum. The signal may be, for example:
wavelength of light;
intensity of signal;
brightness;
the shape of a signal or spectrum;
the presence or absence of spectral bands;
the extinction coefficient of an absorption band;
the $\lambda_{max}$ of an absorption band;
the quantum yield of an emission band; or
the fluorescence anisotropy of an emission band.

The optical signal from an optical reporter molecule may change upon binding of an analyte molecule. The change in optical signal upon binding may be one of the following:
a shift in the center of a spectrum above or below a specified wavelength;
a shift in wavelength of maximum intensity ($\lambda_{max}$);
a change in the size or intensity of the signal;
an increase or decrease in brightness;
a change in the shape of the signal;
the presence or absence of spectral bands;
a change in shape of a spectrum;
a change in the extinction coefficient of an absorption band;
a change in the $\lambda_{max}$ of an absorption band;
a change in the quantum yield of an emission band; and
a change in the fluorescence anisotropy of an emission band.

The term "pixel", as used herein, alone or in combination, refers to an area on an area detector, for example an image sensor, whose signal can be measured independently from other pixels. Area detectors are commonly divided into a two-dimensional grid of pixels, with the size of each pixel, and the count of pixels in the two directions, determined by the area detector manufacturer.

The term "precision", as used herein, alone or in combination, is used to refer to the estimate of error that is associated with a reported or estimated value. A low precision measurement, observation, or estimation is associated with a high degree of uncertainty about the closeness of this number to the actual value. A high precision measurement, observation, or estimation is associated with a low degree of uncertainty about the closeness of this number to the actual value. Precision can often be quantified by the use of error bars on graphs or ranges for numerical values. For example, an estimated value that is reported as 10.5±0.1 indicates that the true value is very likely between 10.4 and 10.6; with a small but nonzero chance that the true value is outside this range.

The terms "protein," "polypeptide," "peptide," and "oligopeptide," are used interchangeably herein and include any composition that includes two or more amino acids joined together by a peptide bond. It will be appreciated that polypeptides can contain amino acids other than the 20 amino acids commonly referred to as the 20 naturally occurring amino acids. Also, polypeptides can include one or more amino acids, including the terminal amino acids, which are modified by any means known in the art (whether naturally or non-naturally). Examples of polypeptide modifications include e.g., by glycosylation, or other-post-translational modification. Modifications which can be present in polypeptides of the present disclosure, include, but are not limited to: acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The term "qualitative analysis", as used herein, alone or in combination, is used to describe a method for determining the absence or presence of an analyte molecule in a sample. In some embodiments, a qualitative analysis method reports the presence or absence of a single molecule of analyte in a sample. In some embodiments, a qualitative analysis method incorrectly reports the absence of analyte in a sample that contains analyte at a level below a certain threshold.

The term "quantitative analysis", as used herein, alone or in combination, is used to describe a method for determining the amount of an analyte molecule in a sample.

The term "recording device", as used herein, alone or in combination, refers to a device for recording an optical signal. In certain embodiments, the optical signal is converted to an electrical signal. In certain embodiments, the recording device is a charge-coupled device ("CCD"). In certain embodiments, the recording device is a complementary metal-oxide semiconductor ("CMOS") device.

The term "reporter molecule", as used herein, alone or in combination, is used to describe a molecule that can report either the presence or absence, or the amount or concentration of, an analyte molecule, and alone or in combination with another reporter molecule, produce a detectable signal in a digital molecular assay. Typically, a reporter molecule will bind to an analyte molecule, and the reporter molecule and analyte molecule complex will differ significantly in one or more spectral properties. Reporter molecules can be antibodies or fragment thereof, nucleic acids, proteins, and peptides, any of which may be chemically or biochemically modified. Reporter molecules can also be chimeric molecules comprising a moiety of biochemical origin and a synthetic moiety; examples include an antibody-functionalized plasmonic nanoparticle and a nucleotide-functionalized plasmonic nanoparticle. Reporter molecules can be aptamers based on either nucleic acids or peptides.

The term "reporter volume", as used herein, alone or in combination, is used to describe the volume of the measurement device in which the reporter molecules are located. The reporter volume may be substantially the same as the sample compartment, or the reporter volume may be smaller. In certain embodiments, the dimension of the reporter volume that is parallel to the optical paths for the reporter molecules will be small. In certain embodiments, the reporter volume will constitute a monolayer.

The term "sample", as used herein, alone or in combination, is used to describe a composition that contains the analyte of interest. A sample will often be in fluid, e.g. aqueous, solution. A sample may be chemical or biological. Blood, plasma, water from a source to be tested, extracts from plant, animal, or human tissue samples, are examples of biological samples. A chemical sample would be one that did not contain material of biological origin, such as a water sample containing petrochemical or industrial waste. Biological samples drawn from an organism can include, but are not limited to, the following: blood, serum, plasma, urine, mucus, saliva, sputum, stool, and other physiological secretions, as well as extracts of tissues, and/or any other constituents of the body which can contain the target particle of interest. Other similar specimens such as cell or tissue culture or culture broth are also of interest.

A biological sample may be fresh or stored (e.g. blood or blood fraction stored in a blood bank). The biological sample may be a bodily fluid expressly obtained for the assays of this invention or a bodily fluid obtained for another purpose which can be sub-sampled for the assays of this invention. In one embodiment, the biological sample is whole blood. Whole blood may be obtained from the subject using standard clinical procedures. In another embodiment, the biological sample is plasma. Plasma may be obtained from whole blood samples by centrifugation of anti-coagulated blood. Such process provides a buffy coat of white cell components and a supernatant of the plasma. In another embodiment, the biological sample is serum. Serum may be obtained by centrifugation of whole blood samples that have been collected in tubes that are free of anti-coagulant. The blood is permitted to clot prior to centrifugation. The yellowish-reddish fluid that is obtained by centrifugation is the serum. In another embodiment, the sample is urine. The sample may be pretreated as necessary by dilution in an appropriate buffer solution, heparinized, concentrated if desired, or fractionated by any number of methods including but not limited to ultracentrifugation, fractionation by fast performance liquid chromatography (FPLC), or precipitation of apolipoprotein B containing proteins with dextran sulfate or other methods. Any of a number of standard aqueous buffer solutions at physiological pH, such as phosphate, Tris, or the like, can be used.

The term "saturation", as used herein, in reference to binding phenomena, refers to a state in which nearly all reporter molecules are bound to analyte molecules. A characteristic of a condition of saturation is that an increase in the concentration of analyte causes a small increase in the degree of binding of reporter molecules.

The term "smartphone" as used herein, refers to a handheld personal computer with a mobile operating system and an integrated mobile broadband cellular network connection for voice, SMS, and internet data communication, and, typically, wi-fi.

The term "tablet computer" or "tablet," as used herein, refers to a thin, flat, portable personal computer, typically with a mobile operating system, LCD touchscreen display, a rechargeable battery, and a wireless (optionally, cellular) communication interface.

Embodiments

The invention is further described by the following embodiments.

Embodiment 1. The disclosure provides a method for determining the presence or concentration of at least one analyte in a sample, comprising:
in an image of a plurality of signals emitted by at least one type of optical reporter molecules incubated with at least one type of analyte molecules;
for each type of optical reporter molecules, determining the number of discrete optical reporter molecules bound to analyte molecules ("bound optical reporter molecules") and the number of discrete optical reporter molecules unbound to analyte ("unbound optical reporter molecules") in the image by individually resolving bound and unbound optical reporter molecules; and,
determining the presence or concentration of analyte from the number of bound optical reporter molecules as a fraction of, or as proportional to a fraction of, the total number of optical reporter molecules.

Embodiment 2. In certain embodiments, the disclosure provides a method for determining the presence or concentration of at least one analyte in a sample, comprising:
in an image of a plurality of signals emitted by at least one type of optical reporter molecules incubated with at least one type of analyte molecules,
for each type of optical reporter molecules, determining the number of discrete optical reporter molecules bound to analyte molecules ("bound optical reporter molecules") and the number of discrete optical reporter molecules unbound to analyte ("unbound optical reporter molecules") in the image by:
in certain regions of the image, individually resolving bound and unbound optical reporter molecules, and
in certain other regions of the image, wherein a group of two or more optical reporter molecules are not resolved, performing a computational or mathematical deconvolution that provides the number of bound optical reporter molecules and unbound reporter molecules in the group; and
determining the presence or concentration of analyte from the number of bound optical reporter molecules as a fraction of, or as proportional to a fraction of, the total number of optical reporter molecules.

Embodiment 3. The method of either of embodiments 1 or 2, wherein the optical reporter molecules are arrayed on a reporter surface.

Embodiment 4. The method of embodiment 3, wherein the optical reporter molecules are arrayed randomly.

Embodiment 5. The method of embodiment 3, wherein the optical reporter molecules are arrayed in a pattern.

Embodiment 6. The method of any of embodiments 1-5, wherein the fraction of bound optical reporter molecules is determined from the number of unbound optical reporter molecules recorded prior to introduction of the sample.

Embodiment 7. The method of any of embodiments 1-6, wherein the concentration of the at least one analyte is determined.

Embodiment 8. The method of any of embodiments 1-7, wherein the sample is a biological or chemical sample.

Embodiment 9. The method of any of embodiments 1-8, wherein the analyte is chosen from:
a nucleotide sequence; and
an antigen.

Embodiment 10. The method of any of embodiments 1-9, wherein the optical reporter molecule comprises a capture element chosen from:
one or more nucleotide sequences binds the analyte; and
an antibody or a fragment thereof that binds the analyte.

Embodiment 11. The method of any of embodiments 1-10, wherein each optical reporter molecule comprises a plasmonic nanoparticle.

Embodiment 12. The method of any of embodiments 1-11, wherein the optical reporter molecule comprises one or more nucleotide sequences functionalized onto one or more plasmonic nanoparticles.

Embodiment 13. The method of any of embodiments 1-11, wherein the optical reporter molecule comprises one or more antibodies functionalized onto one or more plasmonic nanoparticles.

Embodiment 14. The method of any of embodiments 1-13, wherein the signal from the optical reporter molecule is chosen from:
wavelength of light;
intensity of signal;
brightness;
the shape of a signal or spectrum; and
the presence or absence of spectral bands.

Embodiment 15. The method of any of embodiments 1-14, wherein one signal is produced upon binding of analyte to the optical reporter molecule.

Embodiment 16. The method of any of embodiments 1-15, wherein another signal is produced upon binding of analyte to the optical reporter molecule and binding of a second reporter molecule to the analyte.

Embodiment 17. The method of any of embodiments 1-16, wherein the signals produced by the bound optical reporter molecule and the unbound optical reporter molecule are different.

Embodiment 18. The method of any of embodiments 1-17, wherein the bound and unbound optical reporter molecules are individually resolved by:
a shift in the center of a spectrum above or below a specified wavelength;
a change in the size or intensity of the signal;
an increase or decrease in brightness;
a change in the shape of the signal;
the presence or absence of spectral bands; and
a change in shape of a spectrum.

Embodiment 19. The method of any of embodiments 1-18, wherein the signal emitted by the optical reporter molecule is wavelength of light.

Embodiment 20. The method of any of embodiments 1-19, wherein the bound and unbound optical reporter molecules are individually resolved by a shift in the center of a spectrum above or below a specified wavelength.

Embodiment 21. The method of any of embodiments 1-20, wherein at least some of the optical reporter molecules are affixed to a surface (the reporter surface) such that each affixed optical reporter molecule is spatially resolvable.

Embodiment 22. The method of embodiment 21, wherein the affixed optical reporter molecules are arrayed in a grid or an approximation thereof.

Embodiment 23. The method of embodiment 21, wherein each affixed optical reporter molecules is resolvable as one pixel of a recording device.

Embodiment 24. The method of any of embodiments 1-23, wherein active optical reporter molecules and inactive optical reporter molecules emit different optical signals.

Embodiment 25. The method of any of embodiments 1-24, wherein the method determines the number of discrete active optical reporter molecules bound to analyte molecules ("bound active optical reporter molecules") and the number of discrete optical reporter molecules unbound to analyte ("unbound active optical reporter molecules") in the image.

Embodiment 26. The method of any of embodiments 1-25, wherein non-uniform illumination of the sample does not affect the determination of the presence or concentration of analyte.

Embodiment 27. The method of any of embodiments 1-26, wherein the image is recorded at a known illumination wavelength.

Embodiment 28. The method of any of embodiments 1-27, wherein results at any point in the image are normalized to the known illumination.

Embodiment 29. The method of any of embodiments 1-28, wherein intensity measured at an emission wavelength is normalized by illumination intensity at an excitation wavelength at the same location in an image.

Embodiment 30. The method of any of embodiments 1-29, wherein defects in one or more sections of the sensor which recorded the image do not affect the determination of the presence or concentration of analyte.

Embodiment 31. The method of any of embodiments 1-30, wherein one type of optical reporter molecule is used.

Embodiment 32. The method of any of embodiments 1-31, wherein more than one type of optical reporter molecule is used.

Embodiment 33. The method as recited in any of embodiments 1-32, wherein the method employs a sandwich-type assay.

Embodiment 34. The method of any of embodiments 1-33, wherein a first type of optical reporter molecules are affixed to a surface (the reporter surface) such that each affixed optical reporter molecule is spatially resolvable.

Embodiment 35. The method of any of embodiments 1-34, wherein the first type of optical reporter molecules comprises a capture element for an analyte functionalized onto a plasmonic nanoparticle.

Embodiment 36. The method of any of embodiments 1-35, wherein a second type of optical reporter molecules are added with or after the sample.

Embodiment 37. The method of any of embodiments 1-36, wherein the second type of optical reporter molecules comprises a capture element for the analyte functionalized onto a plasmonic nanoparticle.

Embodiment 38. The method of any of embodiments 1-37, wherein the analyte is an antigen.

Embodiment 39. The method of embodiment 38, wherein each optical reporter molecule comprises as the capture element an antibody or a fragment thereof.

Embodiment 40. The method of any of embodiments 1-37, wherein the analyte is a nucleotide sequence.

Embodiment 41. The method of embodiment 40, wherein each optical reporter molecule comprises as the capture element one or more nucleotide sequences complementary to the analyte nucleotide sequence.

Embodiment 42. The method of any of embodiments 1-41, wherein the method is performed on a digital molecular assay system comprising a mobile device.

Embodiment 43. The method of any of embodiments 1-41, performed on the digital molecular assay system of any of embodiments 50-70.

Embodiment 44. A method for determining the presence or concentration of antigen in a sample, comprising:
in an image of a plurality of signals emitted by at least one type of optical reporter molecules comprising antibodies incubated with antigen, determining the number of discrete active antibodies bound to antigen ("bound active antibodies") and the number of discrete active antibodies unbound to antigen ("unbound active antibodies") in the image by individually resolving bound and unbound optical reporter molecules; and, determining the presence or concentration of antigen from the number of bound active antibodies as a fraction of, or as proportional to a fraction of, the total number of active antibodies.

Embodiment 45. The method of embodiment 44, comprising the limitations of any of embodiments 3-11 and 13-39.

Embodiment 46. The method of embodiment 45, performed on the digital molecular assay system of any of embodiments 50-70.

Embodiment 47. A method for determining the presence or concentration of a target nucleotide sequence in a sample, comprising:

in an image of a plurality of signals emitted by:
a) an optical reporter molecule comprising a first capture nucleotide sequence complementary to a first part of the target nucleotide sequence, and
b) the first optical reporter molecule comprising the first capture nucleotide sequence complementary to part of the target nucleotide sequence and a second optical reporter molecule comprising a second capture nucleotide sequence complementary to a second part of the target nucleotide sequence bound to the target nucleotide sequence ("bound complexes"), determining the number of discrete target nucleotide sequences bound to optical reporter molecules comprising the first and second parts of the complementary nucleotide sequence ("bound complexes");

determining the presence or concentration of the target nucleotide sequence as a fraction of, or as proportional to number of bound complexes as a fraction of the total number of optical reporter molecules emitting detectable signals.

Embodiment 48. The method of embodiment 47, comprising the limitations of any of embodiments 3-12 and 13-37.

Embodiment 49. The method of embodiment 48, wherein the system is of any of embodiments 50-70.

Embodiment 50. A digital assay system for determining a concentration of analyte in a sample, comprising:
an image sensor;
a screen capable of displaying an image;
a microprocessor;
memory;
image analysis software stored in the memory and executable by the processor capable of analyzing the data captured by the image sensor and digitally classifying data; and
optionally, a communication interface.

Embodiment 51. The digital assay system of embodiment 50, wherein the image sensor is capable of operating as part of a dark-field microscope.

Embodiment 52. The digital assay system of embodiment 51, wherein the image sensor is a megapixel camera.

Embodiment 53. The digital assay system of any of embodiments 49-52, wherein the image sensor is complementary metal-oxide semiconductor (CMOS) camera.

Embodiment 54. The digital assay system of any of embodiments 49-53, additionally comprising a source of light or other electromagnetic radiation.

Embodiment 55. The digital assay system of any of embodiments 49-54, wherein the light source comprises a light-emitting diode (LED).

Embodiment 56. The digital assay system of any of embodiments 49-55, additionally comprising a sample chamber that is optionally removable.

Embodiment 57. The digital assay system of any of embodiments 49-56, additionally comprising:
a reporter surface made of glass or polymer, to one side of which optical reporter molecules comprising plasmonic nanoparticles functionalized with capture elements have been affixed; and
a waveguide that is suitable for dark-field microscopy in contact with the opposite side of the reporter surface.

Embodiment 58. The digital assay system of any of embodiments 49-57, wherein each affixed optical reporter molecule is spatially resolvable.

Embodiment 59. The digital assay system of embodiment 58, wherein the affixed optical reporter molecules are arrayed in a grid or an approximation thereof.

Embodiment 60. The digital assay system of embodiment 58 or 59, wherein each affixed optical reporter molecules is resolvable as one pixel of a recording device.

Embodiment 61. The digital assay system of any of embodiments 49-60, wherein the capture element is chosen from:
one or more nucleotide sequences binds the analyte; and
an antibody or a fragment thereof that binds the analyte.

Embodiment 62. The digital assay system of any of embodiments 49-61, wherein the analyte is an antigen.

Embodiment 63. The digital assay system of any of embodiments 49-62, wherein each optical reporter molecule comprises as the capture element an antibody or a fragment thereof.

Embodiment 64. The digital assay system of any of embodiments 49-63, wherein the analyte is a nucleotide sequence.

Embodiment 65. The digital assay system of any of embodiments 49-64, wherein each optical reporter molecule comprises as the capture element one or more nucleotide sequences complementary to the analyte nucleotide sequence.

Embodiment 66. The digital assay system of any of embodiments 49-65, wherein the microprocessor, memory, image sensor, software, screen capable of displaying an image, and communication interface are all comprised within a single, portable device.

Embodiment 67. The digital assay system of any of embodiments 49-66, wherein the communication capability is wireless.

Embodiment 68. The digital assay system of any of embodiments 49-67, wherein the single, portable device is chosen from a smartphone and a tablet computer.

Embodiment 69. The digital assay system of any of embodiments 49-68, wherein the single, portable device is a smartphone.

Embodiment 70. The digital assay system of any of embodiments 49-69, additionally comprising a case for positioning the smartphone, sample chamber, and light source in close and stable proximity.

Also provided are devices comprising the elements above.

Embodiment 71. Also provided is a digital assay system of any of embodiments 50-70, which can perform the method of any of embodiments 1-41, 44, 45, 47, and 48.

Embodiment 72. A method for performing a biochemical assay comprising:
incubating antibodies with antigen;

obtaining an image of a plurality of the antibodies;
classifying the antibodies seen in the image as either active or null;
classifying active antibodies as either bound or unbound;
determining the number of bound and unbound antibodies in the image; and,
measuring a concentration of antigen from the number of bound antibodies as a fraction of the number of active antibodies.

Embodiment 73. The method of embodiment 72, where the antibodies are attached to a surface.

Embodiment 74. The method of embodiment 72, wherein the antibodies and antigen are labeled with optical reporter molecules.

Embodiment 75. The method of embodiment 72, wherein the image is obtained with a mobile device camera.

Embodiment 76. A method for performing a biochemical assay comprising:
incubating optical reporter molecules bound to a first part of a short DNA sequence with optical reporter molecules bound to a second part of the short DNA sequence;
obtaining an image of a plurality of the optical reporter molecules;
classifying molecular complexes seen in the image as either active or null;
classifying active molecular complexes as either bound or unbound;
determining the number of bound and unbound complexes in the image; and,
measuring a concentration of a DNA sequence complementary to both the first and second parts of the short DNA sequence from the number of bound complexes as a fraction of the number of active complexes.

Embodiment 77. The method of embodiment 76, where the short DNA sequences are bound to a surface.

Additional embodiments of the above are detailed below.

Applications

The digital molecular assay methods, systems, and devices disclosed herein are useful in a variety of fields and applications. In particular, digital molecular assays would be useful in "the field," that is, in a portable setting. For example, digital molecular assays would be useful in medical assessment and diagnostics and detection of pathogens, particularly in remote areas, areas that are underserved or difficult to access (e.g. due to violent conflict), areas affected by an epidemic, and in other instances where access to traditional assay equipment and/or professionals is limited. They would also be useful within a hospital or clinic, or in a home-visit setting, where they could be performed or used at point of care or bedside.

Digital molecular assays would be equally useful in a veterinary setting as in a medical, whether in a veterinary office, on a ranch or farm, or anywhere animals in need of testing are located. They could also be used in horticultural or agricultural applications to test plants or soil for pathogens or symbiotic microorganisms, or detect other genotypes and phenotypes of interest.

Digital molecular assays could also be used to test water for contamination, e.g., by bacteria, algae, or fungi, or the toxic products thereof; by petroleum or its products and by-products, and industrial waste. Such assays would be useful for food safety testing and for agricultural uses, such as field or processing facility testing for pathogens, toxins, adulterants, contaminants, and pests.

Assays

Many types of biochemical assays are adaptable to the digital molecular assay format disclosed herein. Examples include: immunoassays in which capture and binding of an antigen by an antibody or a fragment thereof; hybridization assays in which one or more segments of DNA or RNA complementary to analyte DNA/RNA of interest is used to capture the analyte; and ligand binding assays in which a binding partner to a receptor, enzyme, or other protein, or vice versa, is used as the capture agent for the partner analyte (e.g., protein or fragment thereof).

It will be appreciated that immunoassays and hybridization assays can employ a sandwich format in which binding partner pairs, e.g. antibodies or cDNA/RNA, to the same analyte molecule, e.g., an antigen or target DNA/RNA, are used. The disclosure thus encompasses binding partner pairs, e.g., antibodies, wherein both antibodies are specific to the same molecule, e.g., the same antigen, and wherein one or both members of the pair comprises an optical reporter molecule as described herein. The combination of multiple capture and reporter elements still comprises a signal-producing arrangement which, while comprising multiple optical reporter molecules, may still itself be termed an optical reporter molecule.

Capture binding partners and detection binding partner pairs, e.g., capture and detection antibody or nucleotide pairs, can be used in the reporter molecule. Thus, although the digital molecular assays disclosed herein allow for label-free detection of analytes, in some embodiments, a heterogeneous assay protocol is used in which, typically, two binding partners, e.g., two antibodies or two sequences of DNA or RNA, are used. One binding partner is a capture partner, usually immobilized on a solid support such as a plasmonic nanoparticle, and the other binding partner is a detection binding partner, typically with a detectable label attached, such as another plasmonic nanoparticle. Antibodies and antibody pairs are commercially available, and can also be designed and prepared by methods well-known in the art.

Reporter molecules can be attached to a reporter surface, either by nonspecific adsorption, or by specific covalent linkage. The loading of reporter molecules will be determined to a large part by the concentration of the reporter molecules in the preparation solution. More concentrated solutions will provide a higher density of reporter molecules, while at the same time increasing the count of clusters of reporter molecules that contain two or more particles. This latter effect is by no means fatal to successful operation: smaller clusters of reporter molecules can be analyzed with curve-fitting techniques discussed below, while larger clusters that are not suitable for these techniques can be flagged as inactive. Considering the conflicting goals of increasing reporter molecule count and maintaining a manageably small number of reporter molecule clusters, a loading of a maximum of about 1 reporter molecule per square micron will prove to be optimal in certain embodiments. For single-molecule detection, a density that would equate to no more than one analyte molecule (bound to optical reporter molecule) per pixel would be useful.

Analysis using sandwich assays can be performed with a multi-step procedure: the reporter surface that has been functionalized with capture molecules is exposed to the analyte. A certain fraction of capture molecules will bind to analyte, depending on analyte concentration. In a second step, the reporter surface is exposed to a solution with detection molecules. Only those capture molecules that have bound to an analyte in the first step will bind to detection molecules in the second step. A clear advantage of this method is that the capture and detection molecules can be chosen so as to optimize the optical signal that is delivered from the capture molecule/analyte/detection molecule assembly, as compared to the unbound capture molecule.

The methods disclosed herein can be used to identify a phenotypic or genotypic state of interest associated with a clinically diagnosed disease state. Such disease states include, for example, cancer, cardiovascular disease, inflammatory disease, autoimmune disease, neurological disease, infectious disease and pregnancy related disorders. Alternatively, states of health can be detected using markers.

The methods disclosed herein can be used to detect genetic variation. The genetic variation herein may include, but is not limited to, one or more substitution, inversion, insertion, deletion, or mutation in nucleotide sequences (e.g., DNA and RNA) and proteins (e.g., peptide and protein), one or more microdeletion, one or more rare allele, polymorphism, single nucleotide polymorphism (SNP), large-scale genetic polymorphism, such as inversions and translocations, differences in the abundance and/or copy number (e.g., copy number variants, CNVs) of one or more nucleotide molecules (e.g., DNA), trisomy, monosomy, and genomic rearrangements. In some embodiments, the genetic variation may be related to metastasis, presence, absence, and/or risk of a disease, such as cancer, pharmacokinetic variability, drug toxicity, adverse events, recurrence, and/or presence, absence, or risk of organ transplant rejection in the subject. For example, copy number changes in the HER2 gene affect whether a breast cancer patient will respond to Herceptin treatment or not. Similarly, detecting an increase in copy number of chromosome 21 (or 18, or 13, or sex chromosomes) in blood from a pregnant woman may be used to as a non-invasive diagnostic for Down's Syndrome (or Patau's Syndrome or Edwards' Syndrome) in an unborn child. An additional example is the detection of alleles from a transplanted organ that are not present in the recipient genome-monitoring the frequency, or copy number, of these alleles may identify signs of potential organ rejection.

Measurement Devices and Systems

The digital molecular assay methods described herein employ a measurement device or system, either of which comprises the parts required for analysis of samples. The measurement device contains a sample compartment, into which samples are introduced, either by direct addition of the sample of interest, or by insertion of a cuvette or slide, which itself contains the sample of interest. The sample compartment further provides a component that contains reporter molecules, whose function is to bind to the analyte of interest and produce an optical signal. For designs which rely on emission methods, the measurement device provides an illumination device for excitation of chromophores contained in the reporter molecules. The measurement device contains a recording device (e.g. an image sensor, e.g. a digital camera), which detects and records the optical signal from the reporter molecules. Finally, the measurement device can contain additional components, such as controls for operation, a device for displaying or reporting analysis results, and an interface with an external computer. The presence of the various optional components, and their specifics, may differ among various designs of measurement devices.

The system or device as a whole can incorporate a mount for orienting the device for convenient sample addition or removal. The system can be coupled to a mobile computing device. The mobile computing device could be a smartphone, handheld computer, tablet computer, or a similar portable computing device. In some examples, the mobile computing device includes all necessary components, such as: a display, a processor, a memory, and program instructions stored in the memory and executable by the processor, to enable highly automated performance of steps such as: (i) introduction of sample, (ii) optical excitation, (iii) optional pre-screening of the sample to evaluate sample quality and optimal exposure time, (iv) recording of an image by the recording device, (v) subtraction of detector bias, if required, (vi) digitization of detector signal, (vii) recording of digital signal in nonvolatile memory, (viii) recycling of detector, if needed, and (ix) processing of digital signal. The functions could further include determining the result of the digital assay, and conveying the result in visual form to the end user.

The use of a smartphone or other mobile computing device as the detection instrument for digital molecular assays allows inexpensive, portable, and multifunctional systems to perform assays in the field, i.e., outside the laboratory. Applications can include point-of-care diagnostic systems for measuring viral loads, nutritional status, disease biomarkers, or environmental contaminants without the need to transport a sample to a central laboratory. Such tests could be performed in private residences, global-health facilities, in law enforcement installations, and medical clinics. The mobile computing device can connect to the internet, which will enable combination of sensor data with patient information and geographical location. Connectivity to an external computation facility can be provided for data interpretation, geographic and demographic mapping, database construction and maintenance, and delivery of notifications to remote medical experts and authorities. Compact, field-operable digital measurement devices will free assays from the requirements for trained technicians in laboratories. Instead, these assays could be performed by anyone, due to the size and affordability of the detection system.

Biosensors

Digital molecular assay systems or devices as disclosed herein comprise elements which may be termed "biosensors." A biosensor is a device that uses biological molecules (e.g., one or more enzymes, antibodies, or nucleotide sequences) to detect the presence of chemicals. Many kinds of biosensors may be used in a digital molecular assay. A biosensor typically consists of a capture component (often termed the "bioreceptor") and a reporter component, ("biotransducer"), together comprising a reporter molecule as disclosed herein, as well as a system which includes a detector, processor, and display, and optionally other elements such as a signal amplifier, magnifying lens, and light source. The interaction between (typically the binding of) the analyte and the capture element produces an alteration in the reporter element, which outputs a measurable physicochemical signal. This interaction produces a signal which indicates the presence or concentration of the target analyte in the sample.

Reporter components as disclosed herein include optical transducers including plasmonic nanoparticles, other localized surface plasmon resonance (LSPR) systems, plasmon scattering systems, photonic crystals, and any other technology that can detect a single molecule and produce an optical signal.

Capture elements may be natural or engineered biomolecules, such as an antibody or fragment (Fab, Fv or scFv) or domain (VH, VHH) thereof, or a nucleic acid (one or more sections of complementary DNA or RNA to the analyte of interest).

The capture element is attached to reporter element, e.g. by functionalization and layered deposition, or entrapment in a matrix, e.g. a hydrogel or xerogel such as sol-gel. The surface of the sensor to which reporter molecules (comprising capture and reporter elements) are attached, termed the "reporter surface," may be, for example, polymer or glass; or glass coated in metal or bearing the metal nanoparticles (e.g. gold or silver; other metals such as titanium, chromium, and copper have also been used) that comprise the reporter element. This surface forms or is aligned along at least one wall of a chamber or flow cell, into or through which the analyte solution is passed.

In an example of a plasmonic nanoparticle biosensor, the chamber or flow cell may be made of glass or polymer; the glass or polymer reporter surface may bear gold nanoparticles functionalized with capture elements, applied via methods known in the art. For analysis with dark field microscopy, light is passed through the edge of the glass or polymer reporter surface, orthogonal to the plane of the reporter surface.

Sample Compartment

The measurement device provides a sample compartment suitable for introduction of a sample of interest. Measurement devices that employ optical measurement techniques will benefit from a sample compartment that is oblong, with one short dimension. The light path for the optical signal from the reporter molecules to the recording device will align parallel with the short dimension. This orientation will minimize absorption and dispersion of the optical signal that would cause problems for longer optical paths. This criterion allows for the use of either prismatic or cylindrical sample compartments.

Reporter Volume

The sample compartment comprises a component, termed the reporter volume, that contains reporter molecules. This component obviates the need to add reporter molecules to the sample of interest, and will instead enable recycling of the reporter molecules. More importantly, the reporter molecules will be held in a substantially stationary arrangement, so that inactive reporter molecules can be identified and recorder previous to clinical use of the measurement device.

In some embodiments, the reporter volume is defined by a physical enclosure that retains reporter molecules within itself. The physical enclosure may be porous, to allow passage of analyte into the reporter volume for contact with the reporter molecule. In some embodiments, the reporter volume is not defined by a physical enclosure; instead, other means can be provided to retain reporter molecules within the reporter volume and keep the reporter molecule stationary.

In certain embodiments, the reporter molecules are associated with a three-dimensional support. In one design, the reporter molecules are covalently bound to the three-dimensional support. Alternatively, the reporter molecules are not covalently bound to the three-dimensional support, but are impregnated in the three-dimensional support in such a manner as to hinder diffusion from the three-dimensional support. In such a design, the reporter molecules are substantially trapped in the three-dimensional support, and are stationary.

Figure 11:
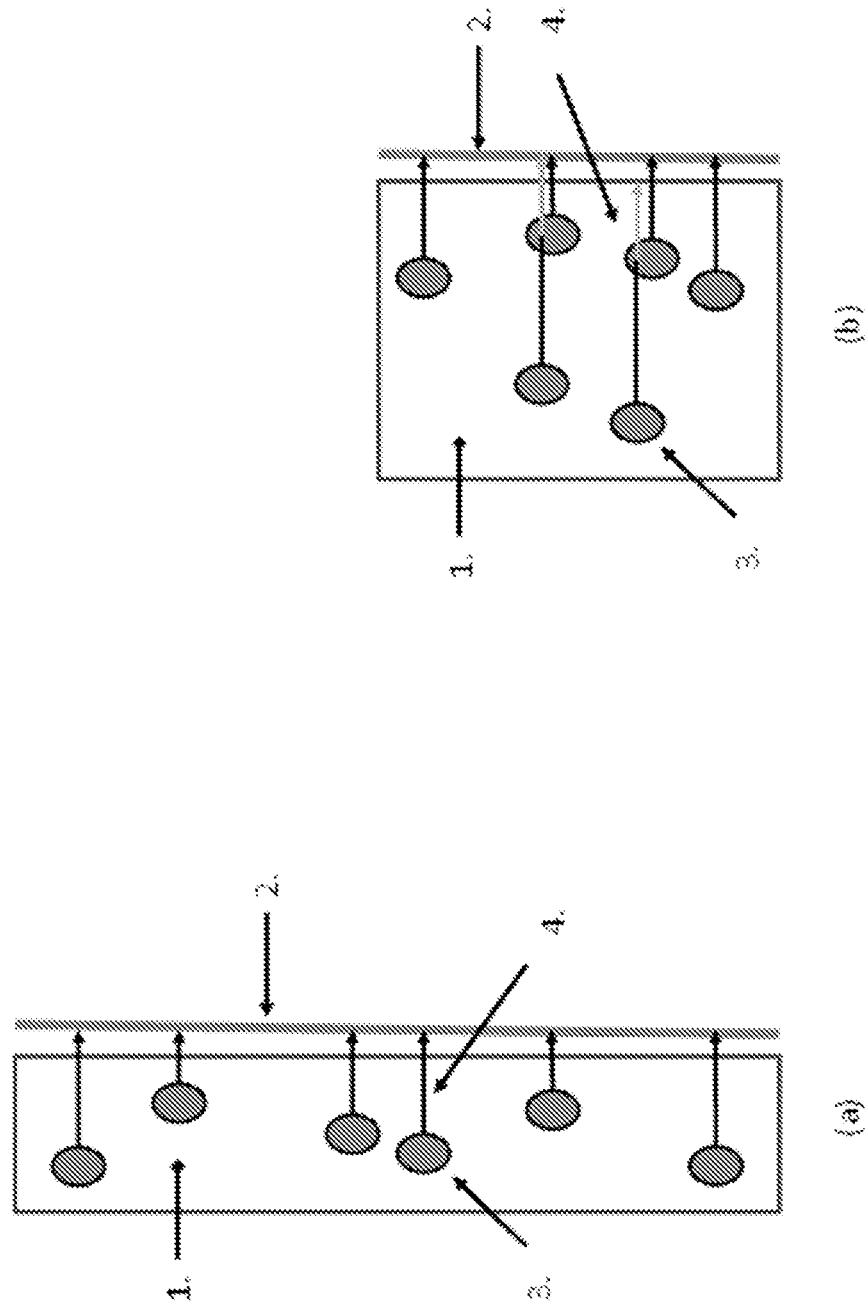
FIG. 11 shows the effect of variations in reporter volume thickness on reporter molecules. In this

The reporter volume will preferably be narrow in the dimension that is perpendicular to the optical pathway for the reporter molecules. This geometry provides an important advantage: the optical pathway from a first reporter molecule is unlikely to encounter a second reporter molecule before arriving at the recording device. This is shown in FIG. 11. A narrow reporter volume is shown in FIG. 11(a), with a recording device to the right, and a non-uniform arrangement of reporter molecules in the reporter volume. It will be seen that, in this geometry, the optical paths from reporter molecules to recording device are well separated. In contrast, a wide reporter volume is shown in FIG. 11(b). In this geometry, at least one reporter molecule overlaps with a second reporter molecule. This overlap is unfavorable for two reasons: (a) the second reporter molecule can partially reabsorb the signal from the first reporter molecule, thus causing error, and (b) identification of inactive reporter molecules, which requires accurate measurement of free and bound signal from reporter molecules, will be made more complicated.

The degree to which optical paths overlap can be estimated from a small number of parameters that define the receptor volume, including the particular distribution of reporter molecules (random, semi-random, aggregated, ordered), the concentration and effective size of the reporter molecules, and the thickness of the reporter volume. In certain embodiments of the disclosure, substantially all optical paths between reporter molecules and the recording device encounter no other reporter molecule. In certain embodiments, substantially all optical paths between reporter molecules and the recording device encounter at most one other reporter molecule.

Figure 12:
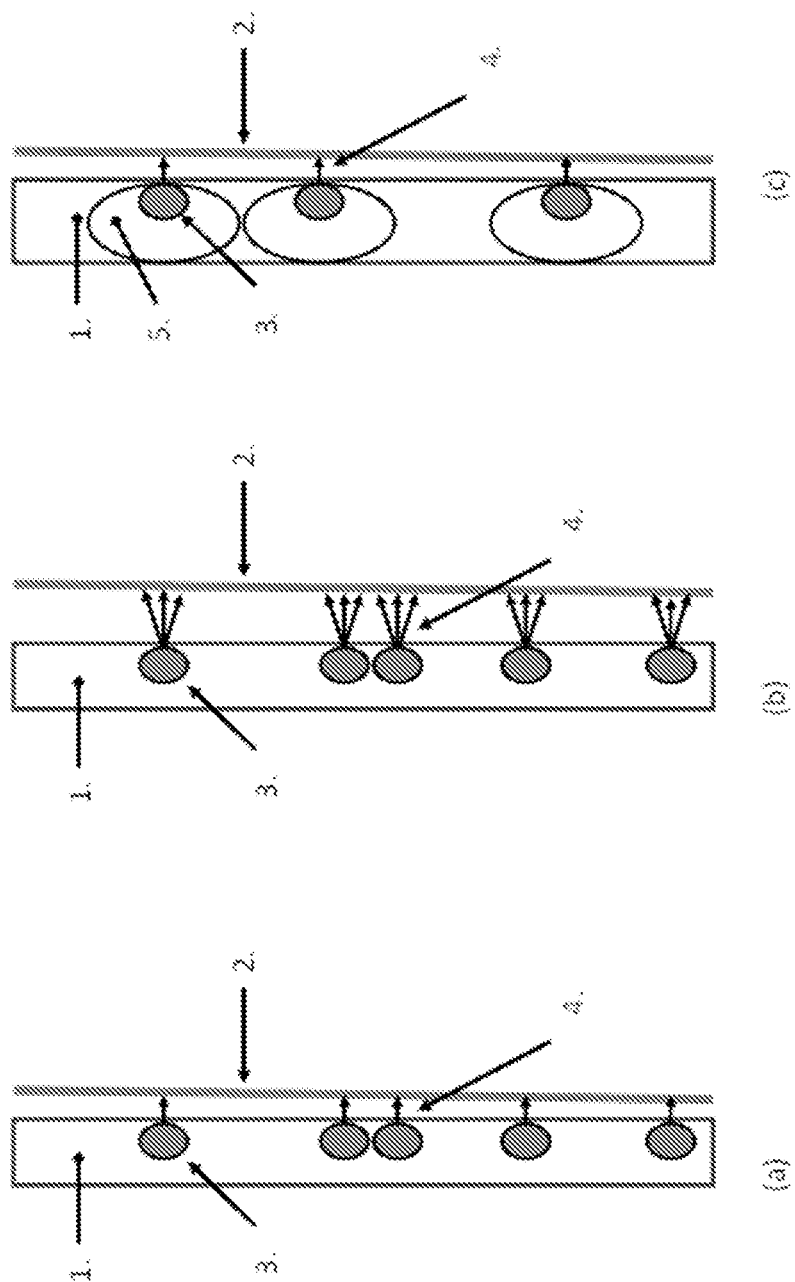
FIG. 12 shows thin reporter volumes and properties thereof. In this

In some embodiments, the reporter volume is sufficiently thin so as to allow for a single layer for the reporter molecules. In this design, overlap of optical paths is not possible, since all reporter molecules are substantially in a plane perpendicular to the optical path, and parallel to the recording device, as depicted in FIG. 12(a). Various monolayer techniques can be used to obtain such a system, such as the use of surface active molecules. Crosslinking of surface active molecules can render the reporter molecules stationary. Discussion of reporter surfaces is presented below in detail.

It should be noted that the preferred distance of closest approach for optical paths of different reporter molecules is determined not only by the size of the reporter molecules (which can determine whether an optical path of one molecule penetrates a second molecule) but also by the spatial resolution of the detector, and in particular the pixel size. Ideally, each reporter molecule will be separated by at least a pixel from any neighboring reporter molecule, in order to most easily identify inactive reporter molecules and observe the optical signal from active reporter molecules. Furthermore, depending on the divergence of the optical paths that enters the recording device, a much larger separation may be desirable. This is shown in FIG. 12(b), for which the distance between reporter volume and recording device has been increased, for clarity, and for which a small, but nonzero divergence of optical signal that enters the recording device. It will be apparent that, even though the reporter molecules do not physically overlap each other, optical signals from closely spaced reporter molecules can potentially overlap.

In order to minimize overlap between optical paths of different reporter molecules, it will be apparent that features and techniques that minimize aggregation of reporter molecules or, conversely, increase separation between reporter molecules, will be advantageous. In one embodiment, individual reporter molecules will be coupled to larger particles, such as microspheres or microparticles, or nanoparticles. Coupling of reporter molecules to larger particles will tend to increase the average distance between reporter molecules, due to the size of the larger particles. This is depicted in FIG. 12(c), in which reporter molecules 3 are attached onto, or within, larger particles 5.

Reporter Surface

In certain embodiments, the sample compartment comprises a reporter surface for attachment of reporter molecules. The reporter surface is oriented perpendicular to the shortest dimension of an oblong sample compartment, in order to minimize the optical path from reporter molecule to recording device. This arrangement of reporter molecules allows easy attachment of reporter molecules to a solid support, and further provides a narrow reporter volume, which is beneficial for the reasons discussed above.

The reporter surface is oriented opposite a window that is substantially transparent to the signal produced by the reporter molecules. The transparent reporter surface can contact a waveguide that is suitable for dark-field microscopy. In certain embodiments, the reporter surface comprises a metallic layer. In certain further embodiments, the metallic layer is suitable for surface plasmon resonance. The reporter surface and transparent window can be located on the two end faces of a prismatic sample compartment, or alternatively on the two end faces of a cylindrical sample compartment. In certain embodiments, the end faces are parallel and proximal, approximating or forming an assay slide or assay chip.

Reporter Molecules

The measurement devices and systems comprise, and the methods disclosed herein employ, a variety of reporter molecules. In one embodiment, a single type of reporter molecule is employed, which will provide a well-behaved binding response to various concentrations of analytes. Alternatively, two or more different reporter molecules having differing affinities for the same analyte, can be employed, which can accommodate a larger range of analyte concentration than a measurement device having a single type of reporter molecule, as described in further detail below. In certain embodiments, two or more different reporter molecules having affinities for different analytes are provided.

The reporter molecules may comprise a chromophore. In certain embodiments, the chromophore has been covalently attached to the reporter molecule; alternatively, it may attach to the reporter molecule via functionalization, e.g. to the surface of a quantum dot or plasmonic nanoparticle. In certain embodiments, the chromophore absorbs electromagnetic radiation. In certain embodiments, the chromophore absorbs electromagnetic radiation in a spectral region chosen from visible and ultraviolet. Alternatively, the chromophore may scatter electromagnetic radiation. In certain embodiments, the chromophore is luminescent. In certain embodiments, the chromophore is fluorescent. In certain embodiments, the chromophore is phosphorescent.

In certain embodiments of the disclosure, the reporter molecules may each comprise a chromophore that provides an optical signal upon binding of analyte. The optical signal may be a change in the extinction coefficient of an absorption band, a change in the $\lambda_{max}$ of an absorption band, a change in the quantum yield of an emission band, a change in the fluorescence anisotropy of an emission band, a shift in the center of a spectrum above or below a specified wavelength, wavelength of maximum intensity ($\lambda_{max}$), a change in the size or intensity of the signal, an increase or decrease in brightness, a change in the shape of the signal, the presence or absence of spectral bands; and a change in shape of a spectrum.

In certain embodiments of the disclosure, the optical signal is caused by an interaction between analyte and chromophore. In certain embodiments, the optical signal is caused indirectly by the binding of analyte to reporter molecule. In certain embodiments, binding of the analyte by the reporter molecule induces a conformational change that affects an absorption or emission property of the chromophore. In certain embodiments, binding of the analyte by the reporter molecule induces an interaction between a chromophore on the analyte and a chromophore on the reporter molecule.

In certain embodiments of the disclosure, the reporter molecule comprises two chromophores. In certain embodiments, binding of an analyte by the reporter molecule induces a geometric change in the reporter molecule that increases a non-radiative interaction between the two chromophores. In certain embodiments, binding of an analyte by the reporter molecule induces a geometric change in the reporter molecule that decreases a non-radiative interaction between the two chromophores. In certain embodiments, the non-radiative interaction is fluorescence quenching. In certain embodiments, the non-radiative interaction is fluorescence energy transfer. In certain embodiments, the non-radiative interaction is phosphorescence energy transfer. In certain embodiments, the non-radiative interaction is plasmon-coupled resonance energy transfer.

In certain embodiments, the chromophore is a plasmonic nanoparticle and/or a quantum dot. The plasmonic nanoparticle and/or quantum dot may be functionalized to bear a capture element. When the capture element is a biological molecule such as an antibody, nucleotide, peptide, or fragment thereof, the chromophore-capture element becomes an optical reporter molecule, and a biosensor. Contact with (e.g., binding of) an analyte, such as an antigen or complementary nucleotide, changes the mass of the induces a change in nanoparticle's spectral properties, due to effects such as electron transfer, energy transfer, plasmon resonance, and changes in the particle's mass and mobility.

Inactive Reporter Molecules

The methods described herein accommodate a certain fraction of reporter molecules that is inactive, i.e., the optical signal from these inactive reporter molecules is either absent or substantially different from the bulk of reporter molecules. This behavior can be due to the failure of a reporter molecule to bind to the analyte. Alternatively, a reporter molecule can bind to the analyte but does not produce an optical signal, or produces an optical signal that is substantially different from the remainder of optical molecules.

In certain embodiments, the system utilizes a nanoparticle as a reporter molecule. The nanoparticle can become inactive on aggregation with other nanoparticles.

In certain embodiments of the disclosure, an inactive reporter molecule comprises individual proteins (including antibodies) that have aggregated, a peptide or protein that has not correctly folded, a peptide or protein that comprises an incorrect residue, a defective chromophore.

The number of inactive reporter molecules can remain substantially constant during the operating lifetime of the measurement device, particularly in cases in which inactive reporter molecules have defective composition. It is also possible that the number of inactive molecules will increase during the operating lifetime of the measurement device, due to chemical deterioration of reporter molecules, particularly photochemical deterioration caused by repeated high intensity exposure to light sources, or aggregation of protein forming part of the reporter molecule.

Inactive reporter molecules can be identified by a change in optical behavior: either their failure to produce an optical signal on exposure to analyte molecules, or the their production of an optical signal on exposure to analyte molecules that is significantly different from the bulk of the reporter molecules.

In certain embodiments, the plurality of reporter molecules is distributed randomly. In certain embodiments, the plurality of reporter molecules comprises aggregates of reporter molecules. In certain embodiments, the plurality of reporter molecules comprises a regular geometric ordering in one or more dimensions. In certain embodiments, each reporter molecule is associated with an exclusion zone, within which no other reporter molecule is located.

Recording Device and Microscope

A recording device is provided to record the optical signal from the reporter molecules. In certain embodiments, the optical signal from the reporter molecules passes through a transparent window of the sample compartment. In certain embodiments, the recording device will be an image sensor, such as a camera. A CMOS (complementary metal-oxide semiconductor) camera, for example, is useful because it can read each pixel individually; additionally, CMOS cameras consume very little power, allowing them to last longer when used as part of a device in the field. Almost all smartphone cameras have CMOS cameras, many with resolution of over 10 megapixels, making them useful in the methods, systems, and devices disclosed herein.

In certain embodiments of the disclosure, the recording device allows the observation of one or more signals from the sample compartment. In certain embodiments, each of a plurality of signals originates from a different region of the sample compartment. In certain embodiments, each signal in the plurality of signals originates from a pixel in a regular geometric grid that spans the sample compartment.

In certain embodiments, the pixels of a recording device are arranged in a rectangular or square array. In certain embodiments, the pixels of a recording device are arranged in a 512×512 square array, a 1024×1024 square array, a 2048×2048 square array, or a 4096×4096 square array. In certain embodiments, the signal from each pixel is recorded separately from all other pixels. In certain embodiments, the signal from 2×2 sets of pixels is binned together.

The measurement device can allow the observation of a plurality of signals from different regions of the plurality of reporter molecules. In certain further embodiments, the different regions of the plurality of reporter molecules are disposed in a regular grid. Alternatively, the individual optical signal from substantially all reporter molecules can be observed without interference from any other reporter molecule.

In certain embodiments, the recording device can capture individual pixels and/or individual reporter molecules. The use of plasmonic nanoparticles or quantum dots as substrates to which capture elements are functionalized facilitates this detection. Used in combination with a magnifying lens, the recording device could detect even smaller signals. Such lenses are well known in the art.

The recording device can use any technique that is known in the art for detection and quantification of reporter molecule/analyte complexes. Recording devices can use optical absorption and emission methods that are paired with the reporter molecule design.

The recording device can make optical absorption measurements. For example, binding with a reporter molecule can be coupled with an enzyme-linked immunosorbent assay (ELISA) that produces a colored product in the presence of an analyte. When the ELISA is functionalized onto a plasmonic nanoparticle or quantum dot, the presence and quantity of analyte would then be reported by, for example, the wavelength, intensity, etc. of an absorption feature; and would yield a signal from each nanoparticle as opposed to a bulk signal.

Alternatively, the optical output could include fluorescence emission from fluorophore either on the reporter molecule or coupled with the reporter molecule that is excited by a light source. The presence and quantity of analyte would then be reported by the intensity of the fluorescence emission. The fluorophore could be proximal to a surface, such as a photonic crystal, such that the fluorescence emission is enhanced. Multiple fluorophores can be employed to tune the fluorescence signal to a desirable outcome. Thus, the optical signal can be modulated by excitation transfer among two or more fluorophores.

Fluorescence and phosphorescence quantum yield, $\lambda_{max}$ shift, and anisotropy are envisioned in this disclosure. For anisotropy measurements, polarizers can be introduced into either the excitation or emission optical pathway, or both. A light source can be coupled with the emission methods. The light source can be a conventional broadband source, light emitting diode, or laser, and can be delivered to the sample either directly or via a wavelength selection device such as a grating, in order to optimize excitation. Light can be directed through a total internal reflection component incorporating a waveguide and forming the base of the reporter surface, thus providing dark field excitation.

In some embodiments, the optical assay medium could include a surface configured for surface-enhanced Raman scattering (SERS). Thus, the optical output could include Raman scattering of the light source by reporter molecules on the SERS surface. The presence and quantity of analyte would then be reported by the intensity of the Raman scattering.

Identification of Inactive Reporter Molecules

Provided herein are methods for identifying inactive reporter molecules, termed "identification method". For certain systems, two solutions, the first free of analyte, and the second with a high concentration of analyte, will be contacted sequentially with the reporter surface. It will be appreciated that these two solutions will cause an absence of analyte binding by reporter molecule, and near saturation of analyte binding by reporter molecule, respectively. Images are recorded using the recording device, and a comparison is made between the images for the analyte-free and analyte-saturated conditions. Reporter molecules that do not meet selectivity criteria are marked as inactive.

In the case of inactivation due to nanoparticle aggregation, identification of inactive reporter molecules will be straightforward. Formation of aggregates will be apparent on visual inspection of the images from the recording device, and will not require the "analyte-free" and "analyte-saturated" procedure outlined above.

The identification method maintains a record for the location of reporter molecules in the measurement device. The location of reporter molecules can be referenced by x/y coordinates, for example, relative to an appropriate geometric grid in the measurement device, or relative to the pixel coordinates on the recorder device. The record of inactive reporter molecules can be maintained on non-volatile computer memory.

The identification method will provide criteria for tagging reporter molecules as inactive. The criteria are set to strike a balance between eliminating poorly behaving reporter molecules from use, while maintaining a sufficiently high count of reporter molecules for the particular accuracy and sensitivity requirements for the measurement device. In order to eliminate bias, and enable automated tagging, a numerical threshold can be chosen, based on the type of optical signal that is observed. By way of example only, a certain reporter molecule may undergo a shift in emission $\lambda_{max}$ on binding to an analyte molecule, and the $\lambda_{max}$ shifts by 20 nanometers (nm) for the bulk of the compounds in this example. A threshold of a 5 nm shift might be chosen for this particular example.

In order to satisfy requirements for accuracy and sensitivity, the numerical threshold can be chosen in order to exclude a certain fraction of reporter molecules. Referring to the previous example, a $\lambda_{max}$ shift of 12 nm may be observed for 95% of the reporter molecules. A threshold $\lambda_{max}$ of 12 nm may then be chosen in order to retain 95% of the reporter molecules as active, and discard 5% of the reporter molecules as inactive.

A variety of criteria can be applied for assigning an inactive status. Importantly, any criteria can be chosen for assigning reporter molecules as inactive. Since the binding of any one reporter molecule is independent of all other reporter molecules, elimination of a reporter molecule from the pool of active reporter molecules does not affect the behavior of the remaining molecules.

If indicated, the identification method described above can be repeated periodically during the operating lifetime of a measurement device. This practice will be particularly beneficial for reporter devices whose performance is susceptible to deterioration over time. Ideally, the identification method will require a minimal amount of operator intervention, with the measurement device automatically performing all required steps. For the case of nanoparticle-based reporter molecules, images can be recorded periodically, and any aggregation that may occur over time can be identified by pattern-matching software.

The identification method can also comprise the steps of subjecting the measurement device to one or more solutions containing intermediate concentrations of analyte. This will be particularly important for quantitative measurement of analyte, for which a range of reporter molecule saturation is envisioned. By use of several solutions, spanning a range of analyte concentrations, a calibration curve can be constructed to better match optical reporting data with concentration of analyte.

A key benefit from the use of spatially resolved signals from a field of reporter molecules is that regions of the recording device that are particularly problematic can be flagged as such, and discarded in subsequent analyses. This includes not only cases for inactive reporter molecules, i.e., improperly folded antibodies, but for any region that presents difficulties. This may include overlapping spots from two or more closely spaced reporter molecules, or reporter molecules whose free and bound states are poorly distinguishable, for whatever reason. Binding of each individual reporter molecule is independent of all others, and discarding a small set of optical signals can improve accuracy or precision, while impacting sensitivity only marginally.

Accuracy/precision/sensitivity

It is expected that accuracy for the disclosed digital measurement methods will be at least as good as for conventional analog methods. The digital measurement methods will minimize or eliminate several sources of error, which by definition is the source of low accuracy. By way of example, one source of error arises from reporter molecules which are inactive: either they do not bind to the analyte molecule, or bind to the analyte molecule and do not provide the expected optical signal. Either situation, if not taken into account, introduces error into the estimation of analyte concentration, since the observed signal will be lower than expected.

It is expected that precision for the disclosed digital measurement methods will be at least as good as for conventional analog measurements. Conventional methods, which observe a bulk signal from the entirety of reporter molecules, can provide precision estimates using various statistical and numerical methods in most, but not all cases.

Consider the system such as that depicted in FIG. 3, which contains a collection of reporter molecules that comprise a chromophore. The observed spectral shift of the bulk signal will be the average of all shifts (if any), and may be quite small, for small analyte concentrations. This shift may be difficult to discern, especially considering the curve broadening due to the different micro-environments surrounding each chromophore.

In contrast, using the digital molecular assay, and observing spectral shifts for each reporter molecule, free reporter molecules will display zero shift, while bound reporter molecules will display full shift. There is no intermediate state. Naturally, not all chromophores will shift by the same value, but the expected value and range can be determined prior to usage in the field. Reporter molecules with outlying values can be discarded as inactive.

It is expected that the signal-to-noise for the disclosed digital methods will be at least as good as conventional methods. For bulk detection, smaller concentrations of analytes will lead to a weaker bulk signal. For digital detection, smaller concentrations of analytes will lead to a smaller number of discrete signals, each of which having the same intensity or value.

Curve Fitting

The individual signals for discrete reporter molecules, shown as simulations in FIG. 8, lend themselves to curve-fitting techniques that can improve the signal-to-noise ratio. The signal from each active reporter molecule will fall in either of two regions of the spectrum, for which idealized noise-free curves (corresponding to the curves in FIG. 8) can be constructed, based on previous knowledge of the reporter molecule. Since each reporter can only be free or bound, the observed signal from a reporter molecule can be assigned as either free or bound. This stands in contrast to many curve-fitting applications, for which superposition of the signals from two or more states, in varying ratios, must be accommodated in order to model the observed signal.

Figure 13:
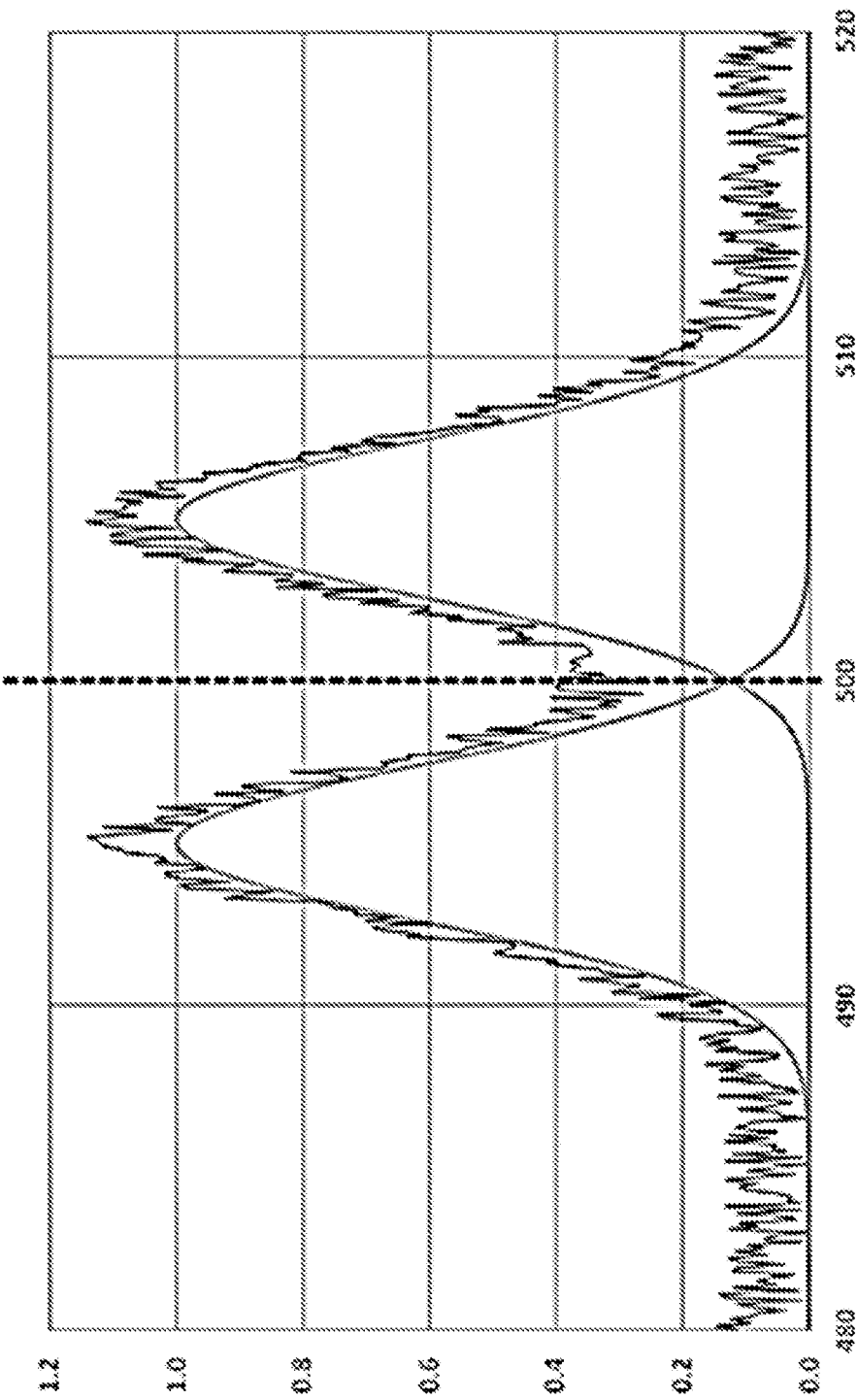
FIG. 13 shows the application of curve-fitting methods to optical spectra. The horizontal axis refers to wavelength in nm, and the vertical axis refers to the intensity of an optical signal.

An example of curve-fitting is shown in FIG. 13. Emission from two signals, shown in gray, is summed, with the simulated addition of "noise" to form a net observed signal, shown in black. The signals are similar to those presented in FIG. 7, and the vertical dashed line in FIG. 12 corresponds to the same delineation of analyte-free and analyte-bound reporter molecule at 500 nm that was discussed in FIG. 8. Curve-fitting techniques can, given the observed signal, estimate the individual signals that combined to give the overall signal. Observed signals that comprise a small number of well-separated individual signals can be evaluated using curve-fitting with high accuracy and precision of curve-fitting. Furthermore, because of the digital nature of binding, i.e., the reporter molecule is either bound to the analyte or is free of analyte, a single reporter molecule can provide only one of two possible signals, corresponding to the analyte-bound and analyte-free states, with no intermediate state possible. In the example shown in FIG. 12, the observed signal can be clearly attributed to two reporter molecules, one with emission below 500 nm, and the other with emission above 500 nm, corresponding to an analyte-bound and an analyte-free reporter molecule. The digital property of this experiment will substantially simplify the curve fitting process.

In addition, the use of curve-fitting techniques can prove advantageous for handling two or more reporter molecules whose optical signals cannot be resolved spatially. In the case of two reporter molecules, whose signals cannot be resolved from each other, four states are possible: (a) both receptors bound; (b) both receptors free; and (c) & (d): one reporter free (the last two states can be expected to have similar but not necessarily identical optical signals). This situation is necessarily more complex than the single reporter molecule; however, it is still very manageable, compared to the optical signal from bulk samples.

Curve-fitting methods can be used for handling two or more reporter molecules whose optical signals are partially resolved spatially, i.e., the optical signals from the two or more reporter molecules is spread unequally across a number of pixels. It can be expected that this scenario will be more common than exact spatial overlap from two or more reporter molecules, especially for recording devices with finely spaced pixels. This scenario can benefit from curve fitting of not a single spectrum from a single pixel (or a summed spectrum from a collection of closely spaced pixels), but instead a collection of individual spectra from a collection of closely spaced pixels, combined with profiles for the (partially overlapping) spots.

Binding Isotherm

The relation between the count of bound reporter molecules and the concentration of analyte, known as the "binding isotherm", is complex and indirect. In short, the ratio of bound/total reporter molecules increases asymptotically to 1 as the concentration of free analyte increases. (Generally, the analyte is present in excess, compared to a much smaller concentration of reporter molecule, so free analyte concentration and total analyte concentration are approximately equal. This approximation will be used throughout this discussion.) A higher affinity reporter molecule will bind to a higher proportion of analyte molecule at any given analyte concentration. Importantly, the total reporter molecule concentration refers only to the active reporter molecule.

Figure 14:
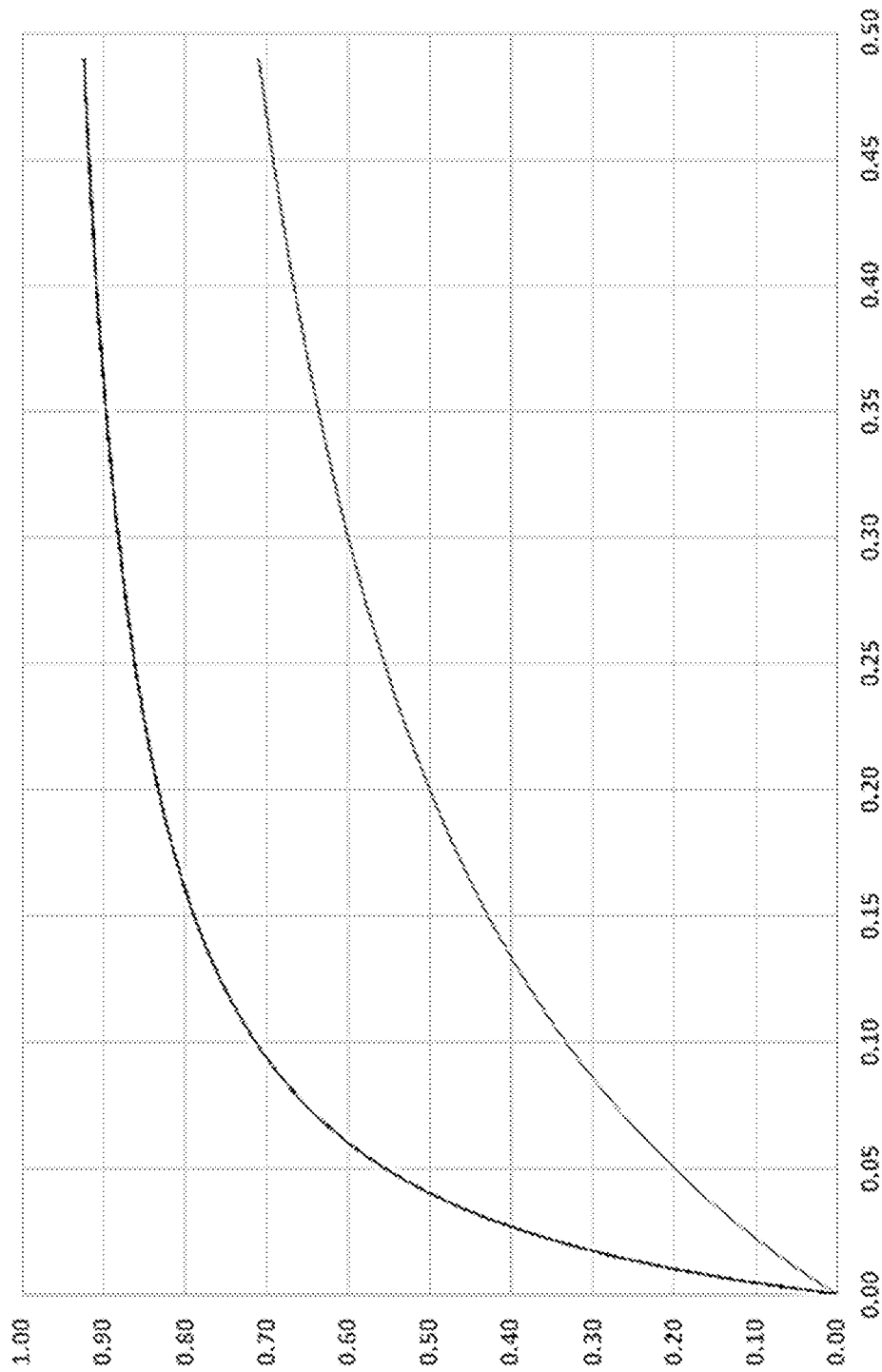
FIG. 14 shows binding isotherm plots for a strongly binding reporter molecule (upper curve) and a weakly binding reporter molecule (lower curve).

Shown in FIG. 14 are two binding isotherm curves. The horizontal axis corresponds to analyte concentration, and the vertical axis corresponds to the ratio of bound/total reporter molecule. The curved lines represent the two binding isotherms, which determine the bound/total reporter molecule ratio at any given analyte concentration. For each curve, the bound/total receptor ratio asymptotically approaches 1 as the analyte concentration increases, and as the reporter molecule approaches saturation, i.e., most every reporter molecule binds to an analyte molecule. The upper, dark curve corresponds to a higher affinity reporter molecule, and the lower curve corresponds to a lower affinity reporter molecule. It will be apparent that the affinity of reporter molecule for analyte will play a large role in the ease of quantifying analytes at different ranges of analyte concentration.

In FIG. 14, the vertical axis (bound/total ratio of reporter molecule) is the dependent variable, and analyte concentration is the independent variable, since the bound/total ratio depends on the analyte concentration. For analytical purposes, the graph is used in reverse; that is, the bound/total ratio is obtained from the experiment, and is located on the vertical axis. From the graph and the binding isotherm curve, the corresponding free analyte concentration is found on the horizontal axis. Visually, this process can be understood by drawing a horizontal line from the observed bound/total ratio on the y-axis to the isotherm curve, and dropping a vertical line to the x-axis, in order to find the analyte concentration. (In practice this process is done mathematically or numerically; however the error analysis still holds.)

Figure 15:
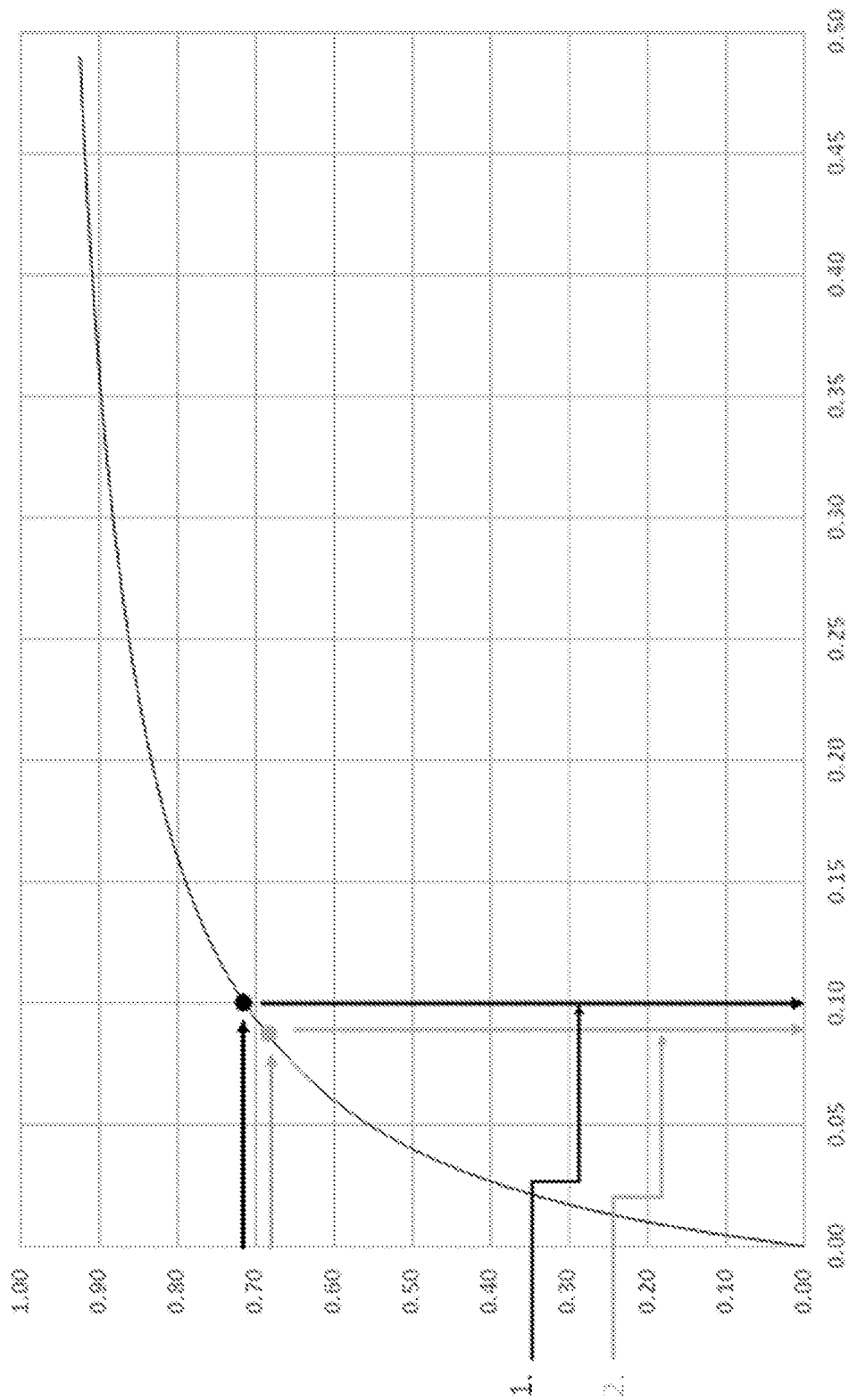
FIG. 15 shows the effect of error on the determination of analyte concentration at low reporter molecule saturation. The horizontal axis is analyte concentration, and the vertical axis is the ratio of bound/total reporter molecule concentration. The dark horizontal and vertical arrows indicated with 1 represent a "correct" determination of reporter molecule concentration and analyte concentration. The light horizontal and vertical arrows indicated with 2 represent an "incorrect" determination of reporter molecule concentration and analyte concentration.

FIG. 15 corresponds to a sample with a free analyte concentration of approximately 0.10, which corresponds to a bound/total ratio of approximately 0.72. This condition is indicated on the binding isotherm as a solid circle. A "correct" determination of 0.72 for bound/total ratio, on the vertical axis, is traced horizontally to the binding isotherm, and down to the horizontal axis. This process is indicated by two black arrows. The result of underestimating the bound/total ratio by about 5% is shown with two gray arrows, with a corresponding grey circle on the binding isotherm.

Figure 16:
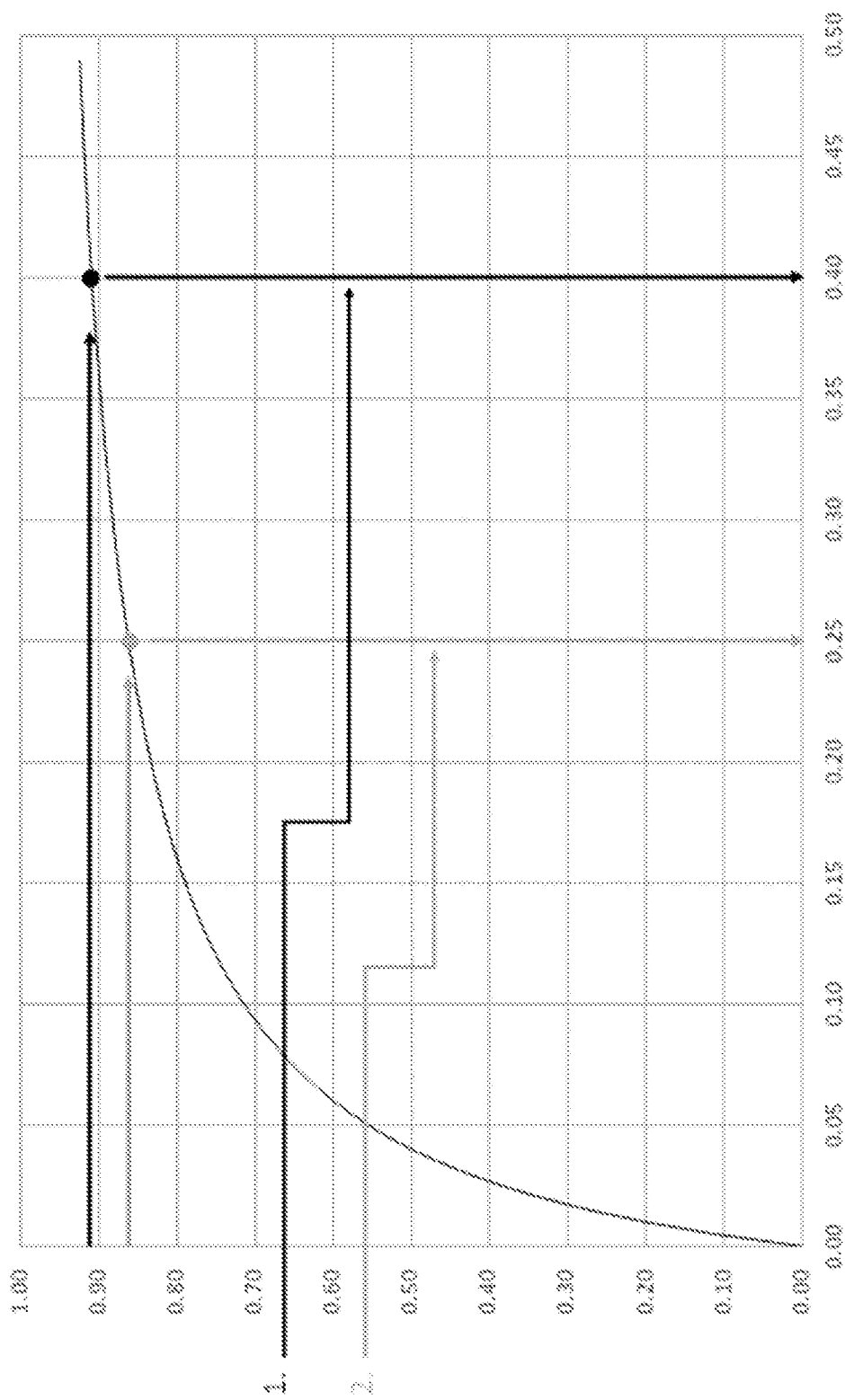
FIG. 16 shows the effect of error on the determination of analyte concentration at high reporter molecule saturation. The horizontal axis is analyte concentration, and the vertical axis is the ratio of bound/total reporter molecule concentration. The dark horizontal and vertical arrows indicated with 1 represent a "correct" determination of reporter molecule concentration and analyte concentration. The light horizontal and vertical arrows indicated with 2 represent an "incorrect" determination of reporter molecule concentration and analyte concentration.

FIG. 16 corresponds to a sample with a higher free analyte concentration of approximately 0.40, corresponding to a bound/total ratio of approximately 0.92, and again marked with a solid circle on the binding isotherm. A correct determination is indicated with two black arrows, as with the previous example. Underestimation of the bound/total ratio by 5% is again shown with gray arrows and gray circle. In this example, a 5% underestimation in bound/total ratio leads to a substantial error of about 40% in analyte concentration. The difference in behavior between FIG. 15 and FIG. 16 is due to the different slope of the binding isotherm graph at the two spots depicted in these two graphs, and this error propagation will be more serious at higher concentrations of analyte, where the binding isotherm curve is flatter.

Analytical devices that utilize molecular binding for quantification of analytes are susceptible to another source of error: in many cases, not all reporter molecules are active for binding of analyte. This causes error in estimation of the bound/total ratio which, as outlined above, can propagate into substantial error in the estimated analyte concentration.

By way of example, consider a measurement device in which 10% of the reporter molecules are inactive. Saturation of reporter molecules will produce only 90% of the expected maximal signal, since 10% of the reporter molecules fail to provide an optical signal (either due to failure to bind analyte, or failure of the receptor/analyte complex to produce an optical signal). Inspection of FIGS. 15 and 16 will reveal the substantial error that will be introduced into measurements, particularly at higher analyte concentrations. To some extent, this error can be addressed by pre-screening measurement devices under saturation conditions to estimate the maximum signal, to be used as a benchmark for future measurements. However, this procedure is not ideal, since full saturation can never be accomplished.

Shown in FIG. 14 are two binding isotherm curves. The upper, dark curve corresponds to a higher affinity reporter molecule. The advantage of using this reporter molecule is that nearly complete saturation can be achieved at relatively low concentration: at 0.40 nM, the reporter molecule is 90% saturated. The disadvantage is that this reporter molecule is useful for quantifying smaller concentrations of about 0.10 nM, since the shallow region of the binding isotherm curve is subject to significant error, as discussed above.

In contrast, the lower, light curve, which corresponds to a lower affinity reporter molecule, is useful to quantify a larger range of sample concentrations, since the curve is relatively steep for the entire range. However, the reporter molecule achieves at most 70% saturation in this range, and determination of the signal corresponding to 100% saturation will be difficult to achieve.

The digital molecular assay methods disclosed herein can include the step of sample dilution, which will improve the precision of estimated analyte concentration by reducing the susceptibility of the measurement to errors in bound/total reporter molecule concentration. By way of example, consider the sample discussed above, whose binding behavior is depicted in FIG. 15. Because of the high degree of reporter molecule saturation, the binding isotherm curve is very shallow in the region around the analyte concentration of 0.40, and determination of analyte concentration is therefore very susceptible to even small errors in bound/total reporter molecule concentration. This ratio is made more precise by digital measurements, as discussed above; however, it would be preferable, from the outset, that the determination of analyte concentration not be as susceptible to errors in bound/total reporter molecule concentration.

Consider the effect of a four-fold dilution of this sample, i.e., addition of sufficient volume of solute in order for the concentration of analyte to drop from 0.40 to 0.10. As a result of this dilution, the binding behavior would now be represented by FIG. 14. Because of the steeper binding isotherm curve in the region around the new analyte concentration of 0.10, determination of analyte concentration is much less susceptible to errors in bound/total reporter concentration.

The sensitivity properties of digital measurements make the step of sample dilution an appealing procedure for improving precision. It will be readily apparent that the precision of a bulk "analog" measurement of bound reporter molecule concentration will suffer upon sample dilution. Going from FIG. 14 to FIG. 13, bound reporter molecule concentration drops from 0.92 to 0.72, representing a 22% drop in bound concentration. A bulk analog signal that is proportional to bound reporter molecule concentration would drop in magnitude by 22%. This drop in magnitude would almost certainly be accompanied by an increase in signal-to-noise, since the magnitude of noise would remain constant. Therefore, the increase in precision due to the binding isotherm effect described above will be counteracted by a decrease in precision due to worsened signal-to-noise in the determination of bound reporter concentration.

In contrast, digital measurements are much less sensitive to this deterioration of signal-to-noise with dilution. As discussed above, a decreased count of bound reporter molecules affects digital measurements differently than analogue measurements. Rather than weakening the bulk signal of analog measurements and thus worsening signal-to-noise, a decreased count of bound reporter molecules will simply reduce the count of discrete optical signals that are received by the reporter device. Importantly, the intensity of each of these discrete optical signals will remain unchanged.

For this reason, dilution methods to improve precision as described above are not accompanied by a decrease in precision due to analog signal-to-noise effects, and will therefore prove beneficial for digital measurements. The measurement methods can include a step of pre-diluting a sample before introduction into the measurement device. Alternatively, the measurement methods can, after reporting an analyte concentration, indicate to the user that a repeat measurement of the sample would improve precision, and can further advise the user on a recommended dilution level.

The measurement methods can include a rapid pre-screen of a sample that is optimized to quickly provide a low-precision estimate of analyte concentration, in order to suggest an optimal dilution.

In many uses that are envisioned for the disclosed methods, thresholds or cutoffs have been established that correspond to critical values. These thresholds or cutoffs can correspond to regulatory levels set by environmental laws, or to critical biomarker levels that correspond to certain health conditions. The measurement methods can adjust the recommended scan parameters and dilution level in order to provide measurement conditions that are adequate for the intended use.

In certain embodiments, the measurement device can provide a mechanism for the automatic dilution of a sample. This can be accomplished by ejecting a fraction of an existing sample, followed by introduction of solute for dilution. This can also be accomplished by introducing a new sample that has been pre-diluted with solute.

In certain embodiments, the recommended dilution level can be calculated by a computing device, either incorporated into the measurement device or connected to the measurement device. The computing device can provide the recommended dilution level to the operator via an interface (such as a display, printout, or synthesized voice report). The computing device can also directly control the measurement device to perform any steps needed to automatically analyze a diluted sample, without the need for user intervention.

In certain embodiments, the thresholds or cutoffs can be pre-set in the computing device, either in the form of firmware, which can be optionally updated in the case a threshold or cutoff changes, or in the form of software. In addition, the operating software can prompt the user for further input on the sample that is being measured. For example, in the case of the measurement of biomarkers, the user can input history parameters for a subject, such as age, weight, gender, and the like, that may alter a threshold or cutoff and that may therefore influence the precision that is required for a given measurement.

EXAMPLES

The invention is further illustrated by the following examples.

Example 1

Plasmonic Sandwich Immunoassay

In one implementation of the digital molecular assay in a dual antibody immunoassay format is described here. Dual antibody immunoassays are widely used in classic clinical assays, and standard antibody pairs for this application can be readily obtained. For detection, plasmon coupling between metal nanoparticles, which will become linked via the analyte in the sandwich immunoassay, provides a robust readout of binding of the analyte molecule to the particles. Plasmon coupling offers a great strength in that the scattering wavelength of the coupled particles can differ substantially from the individual particle scattering wavelengths, leading to distinct color changes easily discerned at the single particle level by color—even on a cell phone camera.

In this example, spherical gold nanoparticles (e.g. between 10 nm and 100 nm in diameter) can work well. For the present purposes, label free detection is unnecessary and detection is achieved by the secondary metal nanoparticle as a signal enhancer. This involves the binding of another nanoparticle (gold) through a second antibody resulting in a plasmonic coupling between the two nanoparticles leading to marked spectral shifts. This strategy has been utilized in the detection of conformational changes in proteins and DNA molecules and will enable easy detection of single analyte binding in images acquired using simple cameras, such as the ones available on cell phones. The enhanced color change due to the second nanoparticle depends on the size of the second nanoparticle as well as the effective distance between the nanoparticles. The interparticle separation (antibody I-analyte-antibody II) expected in our assay will be 20-30 nm and is within the limits of the effective plasmonic coupling. While we typically use 40 nm gold nanoparticles, the dependency of the exponential decay in the plasmonic coupling with interparticle distance on the size of the second nanoparticle (i.e. smaller nanoparticles show rapid decrease in plasmonic coupling compared to larger ones) further allows fine tuning of the spectral shift by using large gold nanoparticles.

Dark-field imaging is one appropriate way to monitor the scattering light from individual particle pairs in the assay. Dark-field microscopy is an optical technique wherein the sample is not directly illuminated. Instead, scattered light is used for the visualization of objects that results in a near-black background intensity leading to a greatly enhanced contrast between objects and background. Indeed, nanoplasmonic materials yield large number of photons without blinking or photobleaching, phenomena that mar fluorescence-based detection that is commonly used in conventional biosensing assays, thus enabling observation of individual particles with a simple optical setup.

The key to the digital molecular assay is individual evaluation of each particle in the field of view. This can be achieved in various ways, but one way involves before and after image comparison, in which the capture particle is first arrayed (randomly or in patterns) on a substrate. The arrayed particles are imaged before introduction of sample providing the 'before' information. The sample is next flowed into the chamber along with the secondary labeled antibody. In a successful analyte capture, a secondary label particle will be associated with the capture particle leading to a defined change in brightness and color. Each particle in the before image will be characterized to determine that it has the expected brightness and color of single capture particles. Any aggregated or otherwise altered particles will be ignored in subsequent analysis. After analyte capture, all images of objects at the locations of good capture particles are analyzed. A statistical criterion for image interpretation is utilized to distinguish failed (e.g. aggregated or nonspecifically bound particles) from clean analyte captures. Background analysis and error correction is enhanced by including non-functionalized particles as fiducial markers. These can be used to sense successful infiltration of solvent, air exposure, or any of a variety of other failure modes that can renders portions of the particle field unusable. In bulk assays, these sorts of errors simply degrade the signal. But in the digital molecular assay format, such errors can be removed ahead of time. In fact, in many single molecule fluorescence imaging experiments it is common for large regions of the field of view to be unusable for various reasons, but with plenty of good molecules in between, the experiments can still run successfully.

Example 2

Plasmonic Hybridization Assay

In a modification of the above example, hybridization of surface-bound nucleic acid probes is combined with plasmonic coupling between nanoparticles to provide a digital molecular assay for nucleic acid analytes. A surface is modified with a first oligonucleotide to which has been attached a first nanoparticle. The surface modification can be performed by noncovalent adsorption, or by covalent binding. The sequence of the first oligonucleotide is chosen to hybridize with a first complementary sequence that is contained in the desired analyte nucleic acid. Exposure of the modified surface then induces hybridization of the analyte with the first short oligonucleotide sequence. At this point, a second oligonucleotide, to which is added a second nanoparticle, is introduced. The sequence of the second oligonucleotide is chosen to hybridize with a second complementary sequence that is contained in the desired analyte nucleic acid, with the first and second complementary sequences sufficiently separated from each other to allow simultaneous hybridization of both the first and the second oligonucleotide sequences.

The supramolecular assembly caused by the hybridization of the analyte nucleic acid with the first and the second oligonucleotide sequences can be designed to bring the first and second nanoparticles into close proximity, as for the sandwich immunoassay described above. Although not strictly necessary for the successful design of this system, adoption of canonical helical structures by the hybridized analyte nucleotide will simplify the molecular geometry, and facilitate the choice of such parameters as sequence length and the nature and placement of attachment to nanoparticles.

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for determining presence or concentration of at least one analyte in a sample, comprising:
   in an image of a plurality of signals emitted by at least one type of optical reporter molecules incubated with at least one type of analyte molecules,
   for each type of optical reporter molecules, determining in the image which optical reporter molecules are active and which are null;
   determining from the active optical reporter molecules the number bound to analyte molecules and the number of active optical reporter molecules unbound to analyte in the image by individually resolving bound and unbound active optical reporter molecules; and
   determining the presence or concentration of analyte from the number of bound active optical reporter molecules as a fraction of, or as proportional to a fraction of, the total number of bound and unbound active optical reporter molecules.

2. The method of claim 1, wherein the optical reporter molecules are arrayed on a reporter surface.

3. The method of claim 2, wherein the optical reporter molecules are arrayed randomly.

4. The method of claim 2, wherein the optical reporter molecules are arrayed in a pattern.

5. The method of claim 2, wherein the fraction of bound optical reporter molecules is determined from the number of unbound optical reporter molecules recorded prior to introduction of the sample.

6. The method of claim 5, wherein the concentration of the at least one analyte is determined.

7. The method of claim 6, wherein the sample is a biological or chemical sample.

8. The method of claim 7, wherein the analyte is chosen from:
   a nucleotide sequence; and
   an antigen.

9. The method of claim 8, wherein the optical reporter molecule comprises a capture element chosen from:
   one or more nucleotide sequences binds the analyte; and
   an antibody or a fragment thereof that binds the analyte.

10. The method of claim 9, wherein each optical reporter molecule comprises a plasmonic nanoparticle.

11. The method of claim 10, wherein the optical reporter molecule comprises one or more nucleotide sequences functionalized onto one or more plasmonic nanoparticles.

12. The method of claim 10, wherein the optical reporter molecule comprises one or more antibodies functionalized onto one or more plasmonic nanoparticles.

13. The method of claim 12, wherein the signal from the optical reporter molecule is chosen from:
wavelength of light;
intensity of signal;
brightness;
the shape of a signal or spectrum; and
the presence or absence of spectral bands.

14. The method of claim 13, wherein one signal is produced upon binding of analyte to the optical reporter molecule.

15. The method of claim 14, wherein a signal is produced upon binding of analyte to the optical reporter molecule and binding of a second reporter molecule to the analyte.

16. The method of claim 15, wherein the signals produced by the bound optical reporter molecule and the unbound optical reporter molecule are different.

17. The method of claim 16, wherein the bound and unbound optical reporter molecules are individually resolved by:
a shift in the center of a spectrum above or below a specified wavelength;
a change in the size or intensity of the signal;
an increase or decrease in brightness;
a change in the shape of the signal;
the presence or absence of spectral bands; and
a change in shape of a spectrum.

18. The method of claim 17, wherein the signal emitted by the optical reporter molecule is wavelength of light.

19. The method of claim 18, wherein the bound and unbound optical reporter molecules are individually resolved by a shift in the center of a spectrum above or below a specified wavelength.

20. The method of claim 19, wherein at least some of the optical reporter molecules are affixed to a surface (the reporter surface) such that each affixed optical reporter molecule is spatially resolvable.

21. The method of claim 20, wherein the affixed optical reporter molecules are arrayed in a grid or an approximation thereof.

22. The method of claim 21, wherein each affixed optical reporter molecule is resolvable as one pixel of a recording device.

23. The method of claim 21, wherein active optical reporter molecules and null optical reporter molecules emit different optical signals.

24. The method of claim 23, wherein non-uniform illumination of the sample does not affect the determination of the presence or concentration of analyte.

25. The method of claim 24, wherein the image is recorded at a known illumination wavelength.

26. The method of claim 24, wherein results at any point in the image are normalized to the known illumination.

27. The method of claim 23, wherein intensity measured at an emission wavelength is normalized by illumination intensity at an excitation wavelength at the same location in an image.

28. The method of claim 23, wherein defects in one or more sections of the sensor which recorded the image do not affect the determination of the presence or concentration of analyte.

29. The method of claim 23, wherein one type of optical reporter molecule is used.

30. The method of claim 29, wherein more than one type of optical reporter molecule is used.

31. The method of claim 30, wherein the method employs a sandwich-type assay.

32. The method of claim 31, wherein a first type of optical reporter molecules is affixed to a surface (the reporter surface) such that each affixed optical reporter molecule is spatially resolvable.

33. The method of claim 32, wherein the first type of optical reporter molecules comprises a capture element for an analyte functionalized onto a plasmonic nanoparticle.

34. The method of claim 33, wherein a second type of optical reporter molecules are added with or after the sample.

35. The method of claim 34, wherein the second type of optical reporter molecules comprises a capture element for the analyte functionalized onto a plasmonic nanoparticle.

36. The method of claim 35 wherein each optical reporter molecule comprises as the capture element an antibody or a fragment thereof.

37. The method of claim 34, wherein the analyte is an antigen.

38. The method of claim 34, wherein the analyte is a nucleotide sequence.

39. The method of claim 38, wherein each optical reporter molecule comprises as the capture element one or more nucleotide sequences complementary to the analyte nucleotide sequence.

40. The method of claim 1, wherein the method is performed on a digital molecular assay system comprising a mobile device.

41. A method for determining presence or concentration of antigen in a sample, comprising:
in an image of a plurality of signals emitted by at least one type of optical reporter molecules comprising antibodies functionalized onto one or more plasmonic nanoparticles incubated with antigen,
for each type of optical reporter molecule, determining in the image which possess active antibodies and which possess null antibodies;
determining the number of active antibodies bound to antigen and the number of active antibodies unbound to antigen in the image by individually resolving bound and unbound optical reporter molecules; and
determining the presence or concentration of antigen from the number of bound active antibodies as a fraction of, or as proportional to a fraction of, the total number of bound and unbound active antibodies.

42. A method for determining presence or concentration of a target nucleotide sequence in a sample, comprising:
in an image of a plurality of signals emitted by
a) an optical reporter molecule comprising a first capture nucleotide sequence complementary to a first part of the target nucleotide sequence and
b) bound complexes comprising a target nucleotide sequence bound to the first optical reporter molecule comprising the first capture nucleotide sequence complementary to part of the target nucleotide sequence and a second optical reporter molecule comprising a second capture nucleotide sequence complementary to a second part of the target nucleotide sequence, determining in the image which optical reporter molecules are active and which are null;

determining the number of active bound complexes, comprising target nucleotide sequences bound to active optical reporter molecules comprising the first and second parts of the complementary nucleotide sequence;

determining the presence or concentration of the target nucleotide sequence as a fraction of, or as proportional to number of active bound complexes as a fraction of the total number of active optical reporter molecules emitting detectable signals.

* * * * *